US012778973B2

(12) United States Patent
Wiertsema et al.

(10) Patent No.: US 12,778,973 B2
(45) Date of Patent: Nov. 3, 2026

(54) NUTRITIONAL COMPOSITIONS FOR GUT BARRIER FUNCTION

(71) Applicant: N.V. Nutricia, Zoetermeer (NL)

(72) Inventors: Selma Paulien Wiertsema, Utrecht (NL); Saskia Adriana Overbeek, Utrecht (NL); Ingrid Brunhilde Renes, Utrecht (NL); Lauriane Emmanuelle Melanie Schwebel, Utrecht (NL)

(73) Assignee: N.V. Nutricia, Zoetermeer (NL)

( * ) Notice: Subject to any disclaimer, the term of this patent is extended or adjusted under 35 U.S.C. 154(b) by 467 days.

(21) Appl. No.: 18/570,652

(22) PCT Filed: Jul. 1, 2022

(86) PCT No.: PCT/EP2022/068341
§ 371 (c)(1),
(2) Date: Dec. 15, 2023

(87) PCT Pub. No.: WO2023/275391
PCT Pub. Date: Jan. 5, 2023

(65) Prior Publication Data

US 2024/0277739 A1 Aug. 22, 2024

(30) Foreign Application Priority Data

Jul. 1, 2021 (EP) .................................... 21183315

(51) Int. Cl.
*A61K 31/702* (2006.01)
*A23L 33/00* (2016.01)
*A23L 33/12* (2016.01)
*A61K 31/201* (2006.01)
*A61P 1/00* (2006.01)

(52) U.S. Cl.
CPC ............ *A61K 31/702* (2013.01); *A23L 33/12* (2016.08); *A23L 33/40* (2016.08); *A61K 31/201* (2013.01); *A61P 1/00* (2018.01)

(58) Field of Classification Search
CPC ...... A61K 31/702; A61K 31/201; A23L 33/40
See application file for complete search history.

(56) References Cited

U.S. PATENT DOCUMENTS

| | | | |
|---|---|---|---|
| 2003/0026860 A1 | 2/2003 | Lasekan et al. | |
| 2008/0064656 A1 | 3/2008 | Van Tol | |
| 2011/0082102 A1 | 4/2011 | Tzortzis et al. | |
| 2012/0058972 A1 | 3/2012 | Tzortzis et al. | |
| 2019/0166898 A1* | 6/2019 | Destaillats | A23L 33/40 |
| 2019/0247469 A1 | 8/2019 | Mcgrath et al. | |

FOREIGN PATENT DOCUMENTS

| | | |
|---|---|---|
| WO | 2005/003329 A1 | 1/2005 |
| WO | 2018/024629 A1 | 2/2018 |
| WO | 2020/229690 A1 | 11/2020 |

OTHER PUBLICATIONS

Newburg et al., Journal of Nutrition, 2016, 146, p. 358-367. (Year: 2016).*

Ghezzal et al: "Palmihic acid damages gut epithelium integrity and initiates inflammatory cytokine production", Biochimica et Biophysica Acta (BBA)—Molecular and Cell Biology of Lipids, Elsevier, Amsterdam, NL, vol. 1865, No. 2, Oct. 21, 2019 (Oct. 21, 2019), XP085975909, ISSN: 1388-1981, DOI: 10.1016/J.BBALIP.2019.158530.

Palomer Xavier et al: "Palmitic and Oleic Acid: The Yin and Yang of Fatty Acids in Type 2 Diabetes Mellitus", Trends in Endocrinology and Metabolism, vol. 29, No. 3, Mar. 1, 2018 (Mar. 1, 2018), pp. 178-190, XP055863233, US, ISSN: 1043-2760, DOI: 10.1016/j.tem.2017.11.009.

* cited by examiner

*Primary Examiner* — Jonathan S Lau
(74) *Attorney, Agent, or Firm* — Ipsilon USA—NLO

(57) ABSTRACT

The present invention concerns nutritional compositions for infants and young children that are high in oleic acid and low in palmitic acid and comprise galacto-oligosaccharides, in particular including beta1,3'-galactosyllactose. The nutritional compositions are particularly advantageous for improving intestinal barrier function.

14 Claims, 3 Drawing Sheets

NUTRITIONAL COMPOSITIONS FOR GUT BARRIER FUNCTION

FIELD OF THE INVENTION

The present invention relates to the field of infant and young child formula and the improvement of the intestinal health.

BACKGROUND OF THE INVENTION

Human milk is considered to be the optimum nutrition for infants. Human milk fed infants for instance have a lower incidence of infections than formula fed infants. Many components in human milk, including immunoglobulins (such as sIgA), interleukin (IL)-1, IL-6, IL-8, IL-10, interferon-γ (IFN-γ), immunocompetent cells, transforming growth factor-β (TGF-β), lactoferrin, nucleotides and human milk oligosaccharides (HMOs) are thought to play a role in protection against infection with pathogens. However there are circumstances that infants are not fed with human milk, and for such circumstances infant or follow on formulas are on the market that aim to substitute human milk. In the design of these formulas it is often the aim to functionally and compositionally mimic the human milk as closely as possible.

Lipids comprise an important part of synthetic nutritional compositions because they provide a substantial part of the energy content. They are a source of essential fatty acids and they are necessary for the intestinal absorption of fat-soluble vitamins. Human milk is very rich in fat. Saturated fatty acids (SFA) are generally the most abundant, accounting for 37-56% of total FAs, with palmitic acid (PA, C16:0) being the predominant one, followed by myristic acid (MA) (C14:0) and stearic acid (SA, C18:0). A total of 10-12% of infants' daily energy supply is provided by PA. Monounsaturated fatty acids (MUFA) are also present, and oleic acid (OA, 18:1 n-9), is the most abundant monounsaturated fatty acid comprising 21-36% of total FAs. Human milk further contains the essential polyunsaturated fatty acids (PUFA) such as the linoleic acid (LA, C18:2 n-3) and alpha linolenic acids (ALA, C18:3 n-6). A striking feature of human milk is the presence of long chain PUFA (LC-PUFA) including DHA (C22:6 n-3), EPA (C22:5 n-3), and AA (C20:4 n-6), typically in amounts of 0.8-1.4 wt. % for n-6 LC-PUFA and 0.3-0.5 wt. % for n-3 LC-PUFA; the amounts vary with diet and stage of lactation. In several recent studies. A lot of health benefits are attributed to the distinctive presence and amounts of LC-PUFA in human milk.

Human milk is also characteristic in the high amount of non-digestible oligosaccharides, and it is the third most abundant components (after lactose and lipid). HMOS are thought to play a role in improving the intestinal microbiota and the intestinal physiology and prevention of infections. Many different the HMOs are present in a concentration of 0.5 to 2.0 g/100 ml and thus far at least 200 structurally different human milk oligosaccharides are known.

Fat blends used to mimic human milk typically are a mixture of vegetable oils including palm oil or cow's milk fat as a source of palmitic acid, sources rich in LA and ALA, and as a source of LC-PUFA microbial oils or animal oil such as fish oil.

Galacto-oligosaccharides (GOS), widely used in infant formula as a source of non-digestible oligosaccharides, were found to protect the intestinal epithelial barrier by maintaining the tight junction network and modulating the inflammatory responses (Akbari et al., The Journal of Nutrition 2015, 145(7):1604-1613).

WO 2020/229690 discloses a method for increasing the intestinal barrier function and/or for prevention and/or treatment of intestinal barrier disruption in a subject, the method comprising administering the trisaccharide Gal (beta 1-3)-Gal (beta 1-4)-Glc to the subject.

WO 2005/122790 discloses a method for stimulating barrier integrity by administering a composition comprising eicosapentaenoic acid (EPA), docosahexaenoic acid (DHA) and arachidonic acid (ARA), and at least two distinct oligosaccharides. The oligosaccharides act indirectly by being fermented to short chain fatty acids (SCFA) by the intestinal microbiota. The SCFA are then the active ingredient that support the intestinal barrier function.

WO 2018/024629 discloses a nutritional composition, for infants and young children in which the sum of the triacylglycerols (TAG) sn-1(3) palmitic acid (PA), myristic acid (MA) and stearic acid (SA) constitutes less than 13.0% of the TAG. The composition promotes absorption of fatty acids and calcium in the gut, improves gut comfort, decreases abdominal pain associated with hard stool formation, promotes regular bowel movements and reduces the incidence and severity of constipation in infants and young children. The composition also promotes bone mineralization, increasing bone strength and bone mineral density.

SUMMARY OF THE INVENTION

In the continuous search to further improve nutrition for infants and young children, the inventors found that adaptation of the amounts of the most abundant fatty acids present in human milk affects the gut barrier function. It was found that the fatty acid oleic acid advantageously improved the epithelial gut barrier function and that the fatty acid palmitic acid did not have such an effect. Interestingly the combination of oleic acid with short chain fatty acid, as produced by fermentation of non-digestible galacto-oligosaccharides, surprisingly showed a strong improved effect on the gut barrier going beyond the effects of the single ingredients, whereas this was not, or to a lesser extent, the case with palmitic acid.

Beta1,3'-galactosyllactose is a species of galacto-oligosaccharides and it was found that fermentation by the microbiota of beta1,3'-galactosyllactose was able to produce the highest amounts of short chain fatty acids. Furthermore this beta1,3'-galactosyllactose also provided the best direct effect on improving the intestinal barrier function. In particular the combination of beta1,3'-galactosyllactose with oleic acid showed a surprising synergistic effect on protecting the intestinal epithelial barrier function.

These findings are indicative of the improved effect of nutritional compositions adapted by reducing levels of palmitic acid and increasing oleic acid and comprising beta1,3'-galactosyllactose, preferably of the improved effect of nutritional compositions adapted by reducing levels of palmitic acid and increasing oleic acid and comprising high amounts of galacto-oligosaccharides including beta1,3'-galactosyllactose. This is of particular benefit for infants and young children as the gut barrier function in infants and young children is more susceptible to disruption because the development of the gut is not yet complete and the developing intestinal microbiota is less stable.

BRIEF DESCRIPTION OF THE DRAWINGS

FIGS. 1A and 1B show the transepithelial electrical resistance (TEER) for different GLs. FIGS. 1C and 1D show the translocation of lucifer yellow (LYF) to the basolateral compartment. TEER was expressed as a percentage of the initial value and LYF was expressed in ng/cm2×h.

FIGS. 1 and 2: alpha3'-GL is Gal (alpha 1-3)-Gal (beta 1-4)-Glc; beta3'-GL is Gal (beta 1-3)-Gal (beta 1-4)-Glc; beta4'-GL is Gal (beta 1-4)-Gal (beta 1-4)-Glc; beta6'-GL is Gal (beta 1-6)-Gal (beta 1-4)-Glc. Data are the mean±s.e. *: $p<0.05$ compared to control, : $p<0.01$ compared to control, *: $p<0.001$ compared to control, ^: $p<0.05$ compared to DON control, ^^$p<0.01$ compared to DON Control, ^^^ $p<0.001$ compared to DON Control.

DETAILED DESCRIPTION

Figure 1A:
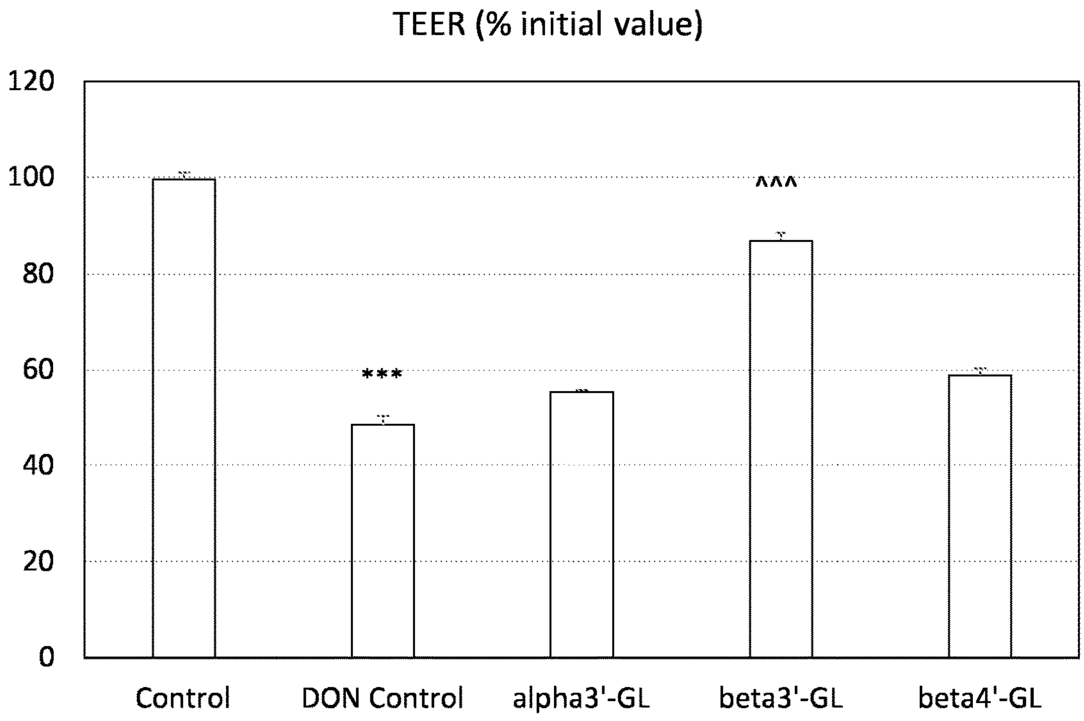
FIG. 1A-1B-1C-1D: Effects of different galactosyllactoses (GLs) on the DON-induced impairment of the Caco-2 cell monolayer integrity.
Figure 1B:
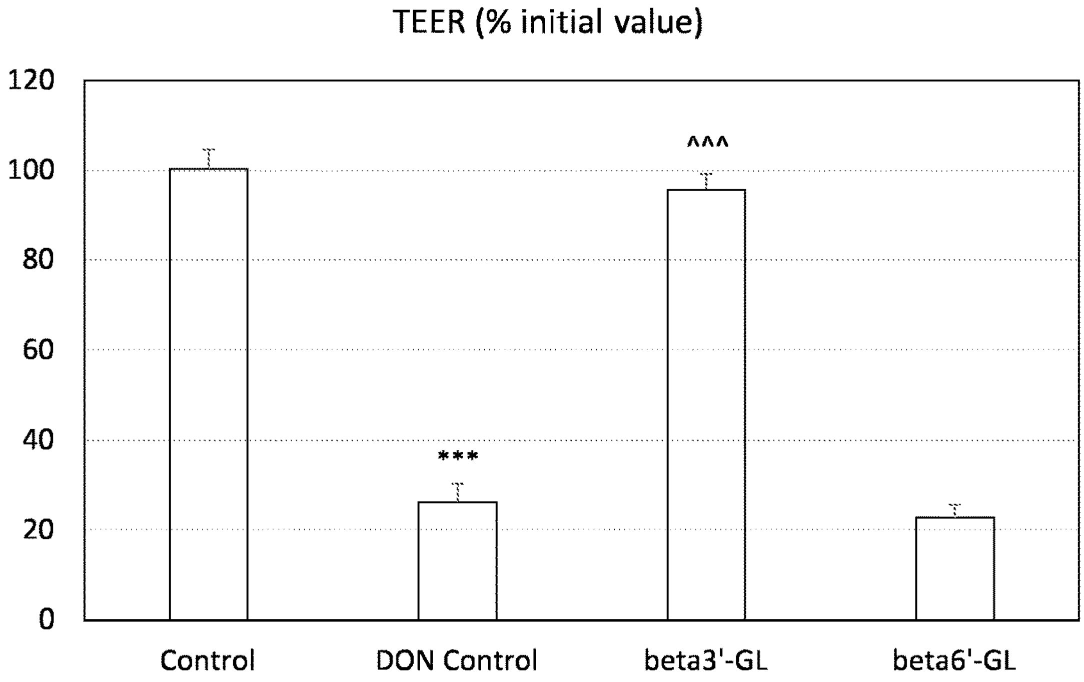
Figure 1C:
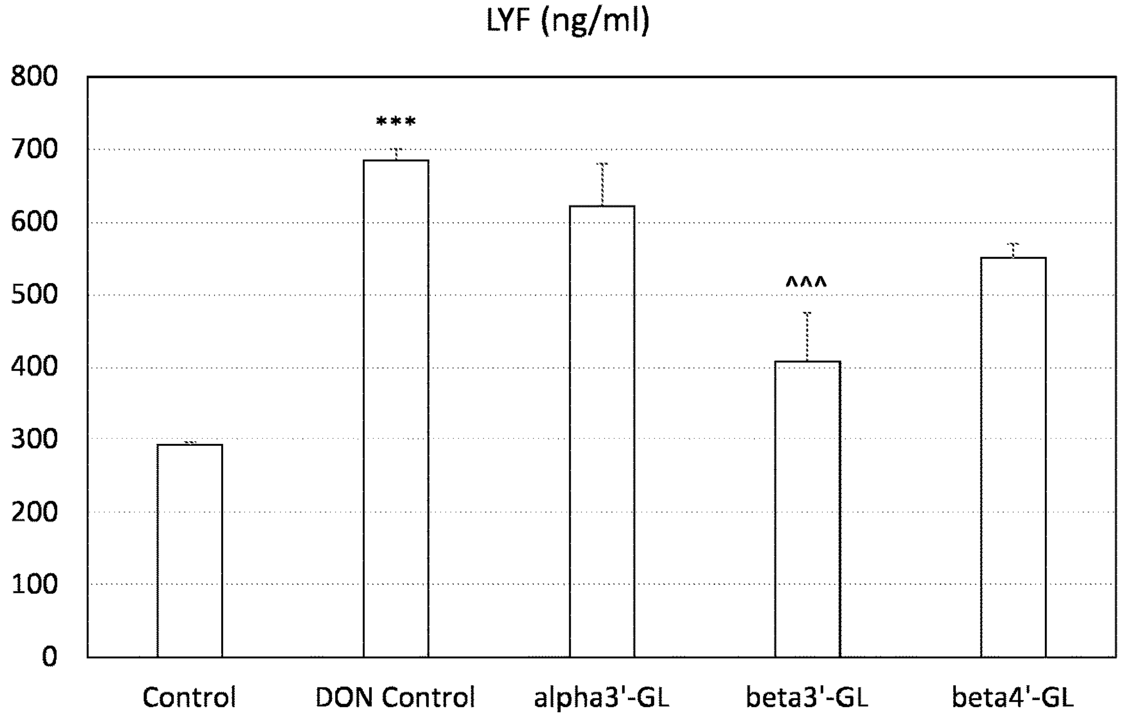
Figure 1D:
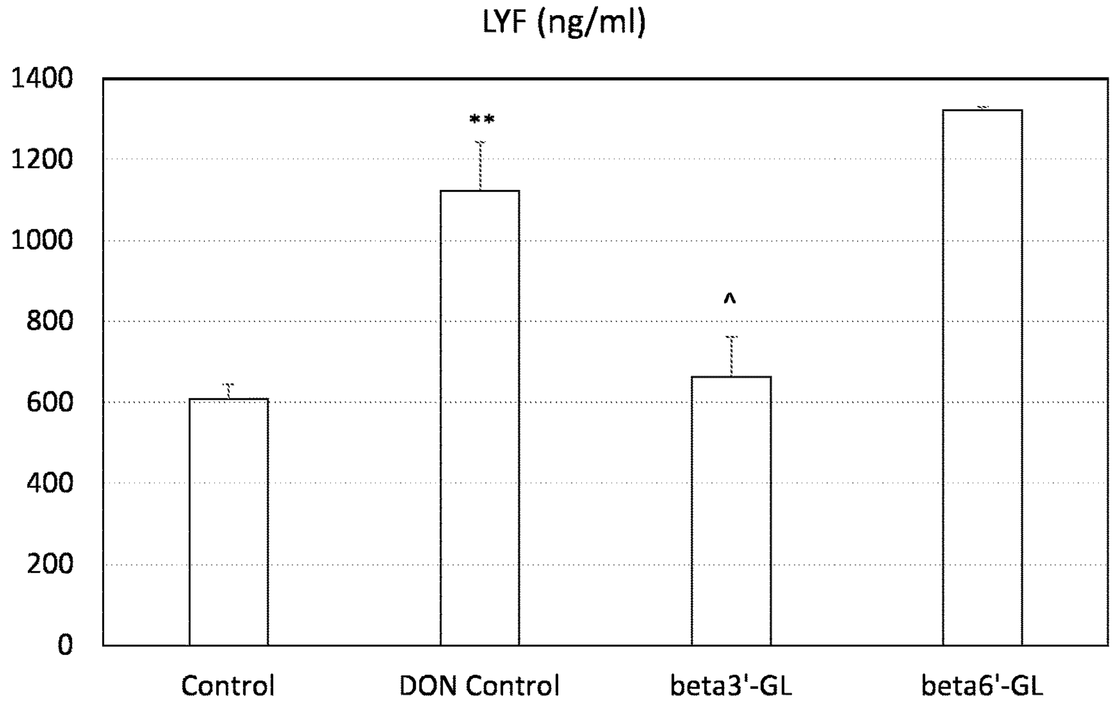

The present invention thus concerns a nutritional composition comprising:

- at least 45 wt. % oleic acid based on total fatty acids,
- no more than 10 wt. % palmitic acid based on total fatty acids,
- a wt/wt ratio of palmitic acid:oleic acid of no more than 1:4.5, and
- at least 0.05 wt. % beta1,3'-galactosyllactose based on total dry weight of the composition.

In a further aspect, the present invention concerns a nutritional composition according to the invention for use in improving intestinal barrier function.

In case improving intestinal barrier function is considered non-therapeutic, the present invention can be worded as a non-therapeutic method for increasing the intestinal barrier function comprising administering a nutritional composition according to the invention to a subject, preferably an infant or young child.

In a further aspect, the present invention concerns a nutritional composition according to the invention for use in treating and/or preventing of intestinal barrier disruption.

In yet a further aspect, the present invention concerns a nutritional composition according to the invention for use in treating and/or preventing intestinal barrier mediated disorders selected from the group consisting of intestinal inflammation, infections originating from the intestine and food allergy.

Fat Blends Low in Palmitic Acid, High in Oleic Acid

The nutritional composition of the present invention comprises lipids. The lipid is mainly in the form of triglycerides and may further comprise non triglyceride lipid components such as phospholipids, glycolipids, diacyl glycerol, monoacylglycerol, cholesterol and free fatty acids. Preferably at least 90 wt. % of the lipid is in the form of triglycerides, more preferably at least 95 wt. %, even more preferably at least 98 wt. %.

Preferably the present composition comprises at least one lipid selected from the group consisting of vegetable lipids. Suitable vegetable oils (herein vegetable lipids and vegetable lipids are used interchangeably) that can be present in a fat blend resulting in the desired fatty acid profile are high oleic acid sunflower, canola oil, coconut oil, sunflower oil, olive oil, soy oil, safflower oil, high oleic safflower oil etc. Preferably the blend does not comprise palm oil and palm kernel oil.

Preferably the present composition comprises a combination of vegetable lipids and at least one oil selected from the group consisting of fish oil, algae oil, fungal oil and bacterial oil. Furthermore soy lecithin can be present as an emulsifier.

The lipid of the present nutritional composition preferably provides 3 to 7 g per 100 kcal of the nutritional composition, preferably the lipid provides 3.5 to 6 g per 100 kcal. When in liquid form, e.g. as a ready-to-feed liquid, the nutritional composition preferably comprises 2.0 to 6.5 g lipid per 100 ml, more preferably 2.5 to 4.0 g per 100 ml. Based on total dry weight the present nutritional composition preferably comprises 15 to 45 wt. % lipid, more preferably 20 to 30 wt. %.

The nutritional composition is characterized in that it has a fatty acid profile with low palmitic acid when compared to human milk and an increased level of oleic acid. In particular the level of palmitic acid present in the sn-1,3 position of the triglyceride molecule is low. Palmitic acid esterified in the sn-1,3 position of the triglycerides, as found in natural vegetable oils and in standard infant formulas, was found to be less desirable as the free palmitic acid formed upon digestion by lipase was found to have no effect on the intestinal epithelia barrier function whereas oleic acid improved the barrier resistance. Besides that, with palmitic acid, the action between the short chain fatty acids, being the metabolites formed upon the fermentation of galacto-oligosaccharides, was not synergistic, and less than observed with oleic acid. In addition the advantageous action between galacto-oligosaccharides that directly protect the intestinal barrier function was unexpectedly more pronounced in the presence of oleic acid than in the presence of palmitic acid.

The nutritional composition of the invention comprises palmitic acid, in an amount of not more than 10 wt. % with respect to total fatty acids. Preferably the amount of palmitic acid is in the range of 3 to 10 wt. % based on total fatty acids, more preferably 3 to 7 wt. %. Expressed per 100 kcal preferably the nutritional composition of the invention comprises palmitic acid in an amount of not more than 0.48 gram palmitic acid per 100 kcal; more preferably the amount of palmitic acid is 0.15 to 0.48 gram palmitic acid per 100 kcal, even more preferably 0.15 to 0.34 gram palmitic acid per 100 kcal. Expressed per 100 ml preferably the nutritional composition of the invention comprises palmitic acid in an amount of not more than 0.32 gram palmitic acid per 100 ml; more preferably the amount of palmitic acid is 0.10 to 0.32 gram palmitic acid per 100 ml, even more preferably 0.10 to 0.22 gram palmitic acid per 100 ml.

In a preferred embodiment, at least 90 wt. % of the lipid of the nutritional composition of the invention is in the form of triglycerides, more preferably at least 95 wt. %, even more preferably at least 98 wt. %, and the nutritional composition preferably comprises palmitic acid at the sn 1 or 3 position in the triglyceride of no more than 9 wt. % with respect to total fatty acids; more preferably the amount of palmitic acid is 2.5 to 9 wt. % based on total fatty acids, even more preferably 2.5 to 6.5 wt. %. Expressed per 100 kcal preferably for this embodiment the nutritional composition of the invention comprises palmitic acid at the sn 1 or 3 position in the triglyceride in an amount of not more than 0.44 gram palmitic acid at the sn 1 or 3 position in the triglyceride per 100 kcal; more preferably the amount of palmitic acid at the sn 1 or 3 position in the triglyceride is 0.12 to 0.44 gram palmitic acid at the sn 1 or 3 position in the triglyceride per 100 kcal, even more preferably 0.12 to 0.31 gram palmitic acid at the sn 1 or 3 position in the triglyceride per 100 kcal. Expressed per 100 ml for this embodiment preferably the nutritional composition of the invention comprises palmitic acid at the sn 1 or 3 position in the triglyceride in an amount of not more than 0.29 gram palmitic acid at the sn 1 or 3 position in the triglyceride per 100 ml; more preferably the amount of palmitic acid at the sn 1 or 3 position in the triglyceride is 0.08 to 0.29 gram palmitic acid at the sn 1 or 3 position in the triglyceride per 100 ml, even more preferably 0.08 to 0.21 gram palmitic acid at the sn 1 or 3 position in the triglyceride per 100 ml.

The nutritional composition of the invention comprises oleic acid an amount of at least 45 wt. % based on total fatty acids; preferably the amount of oleic acid is 45 to 60 wt. % based on total fatty acids, more preferably 48 to 55 wt. %. Expressed per 100 kcal preferably the nutritional composition of the invention comprises oleic acid in an amount of at least 2.2 gram oleic acid per 100 kcal; more preferably the amount of oleic acid is 2.2 to 2.9 gram oleic acid per 100 kcal, even more preferably 2.3 to 2.7 gram oleic acid per 100 kcal. Expressed per 100 ml preferably the nutritional composition of the invention comprises oleic acid in an amount of at least 1.4 gram oleic acid per 100 ml; more preferably the amount of oleic acid is 1.4 to 1.9 gram oleic acid per 100 ml, even more preferably 1.5 to 1.8 gram oleic acid per 100 ml.

In a preferred embodiment the total amount of the saturated fatty acids stearic acid and palmitic acid is limited as in addition to palmitic acid also stearic acid may affect the intestinal barrier integrity. The nutritional composition of the invention preferably comprises the sum of stearic acid and palmitic acid in an amount of not more than 12 wt. % with respect to total fatty acids; more preferably the amount of the sum of stearic acid and palmitic acid is in the range of 4 to 12 wt. % based on total fatty acids, even more preferably 4 to 8 wt. %. Expressed per 100 kcal preferably the nutritional composition of the invention comprises the sum of stearic acid and palmitic acid in an amount of not more than 0.58 gram per 100 kcal; more preferably the amount of the sum of stearic acid and palmitic acid is 0.19 to 0.58 gram per 100 kcal, even more preferably 0.19 to 0.39 gram per 100 kcal. Expressed per 100 ml preferably the nutritional composition of the invention comprises the sum of stearic acid and palmitic acid in an amount of not more than 0.38 gram per 100 ml; more preferably the amount of the sum of stearic acid and palmitic acid is 0.13 to 0.38 gram per 100 ml, even more preferably 0.13 to 0.26 gram per 100 ml.

In another preferred embodiment the total amount of the saturated fatty acids stearic acid, myristic acid and palmitic acid is limited as in addition to palmitic acid also stearic acid and myristic may affect the intestinal barrier integrity. The nutritional composition of the invention preferably comprises the sum of stearic acid, myristic and palmitic acid in an amount of not more than 17 wt. % with respect to total fatty acids; more preferably the amount of the sum of stearic acid, myristic and palmitic acid is in the range of 5 to 17 wt. % based on total fatty acids, even more preferably 5 to 12 wt. %. Expressed per 100 kcal preferably the nutritional composition of the invention comprises the sum of stearic acid, myristic and palmitic acid in an amount of not more than 0.82 gram per 100 kcal; more preferably the amount of the sum of stearic acid, myristic and palmitic acid is 0.24 to 0.82 gram per 100 kcal, even more preferably 0.24 to 0.58 gram per 100 kcal. Expressed per 100 ml preferably the nutritional composition of the invention comprises the sum of stearic acid, myristic and palmitic acid in an amount of not more than 0.54 gram per 100 ml; more preferably the amount of the sum of stearic acid and palmitic acid is 0.16 to 0.54 gram per 100 ml, even more preferably 0.16 to 0.38 gram per 100 ml.

The nutritional composition of the invention preferably has a wt/wt ratio of palmitic acid to oleic acid of no more than 1:4.5, more preferably in the range of 1:10 to 1:4.5 and even more preferably in the range of 1:8 to 1:7. To be clear, with the requirements that the nutritional composition comprises at least 45 wt. % oleic acid based on total fatty acids and at most 10 wt. % palmitic acid based on total fatty acids, it follows that there is at least 4.5 times as much oleic acid than palmitic acid, so the requirement a wt/wt ratio of palmitic acid:oleic acid of no more than 1:4.5 is the same as a wt/wt ratio of oleic acid:palmitic acid of at least 4.5:1, thus weight oleic acid divided by weight palmitic acid 4.5.

In a preferred embodiment at least 90 wt. % of the lipid of the nutritional composition of the invention is in the form of triglycerides, more preferably at least 95 wt. %, even more preferably at least 98 wt. %; and the nutritional composition preferably has a wt/wt ratio of palmitic acid at the sn 1 or 3 position in the triglyceride to oleic acid of no more than 1:5, more preferably in the range of 1:11 to 1:5 and even more preferably in the range of 1:9 to 1:7.5.

Preferably the nutritional composition comprises the essential fatty acids alpha-linolenic acid (ALA), linoleic acid (LA). Preferably the nutritional composition comprises 300-1500 milligram (mg) LA per 100 kcal, more preferably 500-1200 mg LA per 100 kcal. Preferably the nutritional composition comprises 30-120 mg LA per 100 kcal, more preferably 50-100 mg LA per 100 kcal. Preferably the ratio of LA:ALA is in the range of 5:1 to 15:1, more preferably the ratio of LA:ALA is in the range of 8:1 to 12:1.

The present composition preferably comprises long chain poly-unsaturated fatty acids (LC-PUFA). LC-PUFA are fatty acids or fatty acyl chains with a length of 20 to 24 carbon atoms, preferably 20 or 22 carbon atoms, comprising two or more unsaturated bonds. Preferably the composition comprises at least one, preferably two, more preferably three LC-PUFA selected from docosahexaenoic acid (DHA), eicosapentaenoic acid (EPA) and arachidonic acid (ARA). These LC-PUFA were found to improve the gut barrier function and may therefore be particularly advantageously combined with beta1,3'-galactosyllactose in order to further improve the gut barrier. This combination has unexpected advantageous effects and preferably works synergistically. Preferably the composition comprises an elevated amount of such LC-PUFA. Preferably the sum of ARA, EPA and DHA is at least 0.8 wt. %. based on total fatty acids. More preferably above 1.0 wt. %. Preferably the amount of these LC-PUFA is not more than 5.0 wt. %, based on total fatty acids. It is further preferred that the amount of these LC-PUFA is in the range of 0.8-5.0 wt. %, more preferably 0.8-1.5 wt. %, even more preferably 1.1-5.0 wt. %, based on total fatty acids. This is considered most optimal range to be used in infant formula for improvement of gut barrier function.

Preferably the amount of DHA is at least 0.4 wt. %, preferably at least 0.5 wt. % based on total fatty acids. Preferably the amount of DHA is not more than 1.0 wt. % based on total fatty acids. Preferably the nutritional composition comprises an amount of EPA of at least 0.09 wt. %, preferably at least 0.10 wt. %, based on total fatty acids, and preferably not more than 0.40 wt. %. Preferably the nutritional composition comprises an amount of ARA of at least 0.25 wt. % based on total fatty acids, more preferably at least 0.50 wt. % and preferably not more than 1.00 wt. %.

Preferably the nutritional composition comprises DHA in amount of 0.4 to 1.0 wt. % based on total fatty acids, and EPA in an amount of 0.09 to 0.40 wt. % based on total fatty acids. More preferably, the nutritional composition comprises DHA in amount of 0.5 to 0.7 wt. % based on total fatty acids, and EPA in an amount of 0.1 to 0.2 wt. % based on total fatty acids. It is particularly preferred that the nutritional composition comprises DHA in amount of more than 0.5 wt. % based on total fatty acids, and EPA in an amount of more than 0.1 wt. % based on total fatty acids.

Preferably the nutritional composition comprises DHA in amount of 19 to 49 mg/100 kcal and EPA in an amount of 4.4 to 19 mg/100 kcal. More preferably the nutritional composition comprises DHA in an amount of 24.2 to 33.9 mg/100 kcal and EPA in an amount of 4.8 to 9.7 mg/100 kcal. Most preferably the nutritional composition comprises DHA in amount of about 24 mg/100 kcal and EPA in an amount of about 5 mg/100 kcal. In these embodiments the presence of ARA is optional. If present, the amount of ARA is preferably 12.5 to 50 mg, more preferably 25 to 33.5 mg and most preferably about 25 mg per 100 kcal.

Preferably the weight ratio of DHA/ARA is from 0.9 to 2. Preferably the weight ratio of DHA/EPA/ARA is 1: (0.19-0.7):(0.9-2.0). Such amounts and/or ratios of DHA, EPA and ARA are optimal for further improving the gut barrier function. Suitable sources of these LC-PUFA are e.g. fish oil and oil from *Mortierella alpina.*

Beta1,3'-Galactosyllactose and Galacto-Oligosaccharides

The nutritional composition comprises the trisaccharide Gal-(beta 1,3)-Gal-(beta 1,4)-Glc, herein also referred to as beta 1,3'-galactosyllactose or beta3'-GL. It was found that in particular the combination of beta1,3'-galactosyllactose with oleic acid showed a surprising synergistic effect on protecting the intestinal epithelial barrier function, in particular under conditions of challenges such as in a model where the gut barrier is disrupted by the toxin DON, deoxynivalenol. This effect is specific for the combination with oleic acid as it was not observed with palmitic acid. Beta1,3'-galactosyllactose is commercially available (Carbosynth) and/or can be obtained as further explained below. The nutritional composition comprises at least 0.05 wt. % beta1,3'-galactosyllactose based on total dry weight of the composition, preferably at least at least 0.10 wt. % based on total dry weight of the composition.

The nutritional composition preferably comprises galacto-oligosaccharides. These galacto-oligosaccharides are non-digestible and are fermented by the intestinal microbiota to yield short chain fatty acids. The short chain fatty acids formed improve the intestinal barrier, and it was now found that in combination with the oleic acid, which is abundant in human milk, a synergistic effect on gut barrier was observed, whereas this effect was not observed with palmitic acid, also abundant in human milk. The nutritional composition preferably comprises at least 1.5 wt. % galacto-oligosaccharides based on total dry weight of the nutritional composition. The nutritional composition preferably comprises galacto-oligosaccharides including the trisaccharide Gal-(beta 1,3)-Gal-(beta 1,4)-Glc, herein also referred to as beta1,3'-galactosyllactose or beta3'-GL. In other words, the beta 1,3'-galactosyllactose is part of galacto-oligosaccharides (GOS). It was found that beta3'-GL is particularly effective in improving the intestinal barrier. This is achieved by a direct effect on the gut barrier in a model where the gut barrier is disrupted by the toxin DON, deoxynivalenol. Furthermore it was found that beta3'-GL fermentation is the most efficient, yielding the fastest and highest amount of short chain fatty acids, in particular acetic acid, that is indicative of an improved effect on the intestinal barrier.

A suitable way to form GOS is to treat lactose with beta-galactosidases. Dependent on the specificity of the enzyme used, a galactose unit is hydrolysed from lactose and coupled to another lactose unit via a beta-linkage to form a trisaccharide. A galactose unit may also be coupled to another single galactose unit to form a disaccharide. Subsequent galactose units are coupled to form oligosaccharides. The majority of such formed oligosaccharides have a degree of polymerization (DP) of 7 or lower. Depending on the enzyme these linkages between the galactose residues can be predominantly beta1,4', beta1,6' or beta1,3'.

A suitable way to prepare beta1,6' and/or beta1,4' GOS is by using the beta-galactosidase from *Bacillus circulans*. A commercially available source of BGOS is Vivinal-GOS from FrieslandCampina Domo (Amersfoort, The Netherlands). Vivinal-GOS comprises BGOS mainly with DP2-8 (peak at DP3) and mainly with beta1,4' and beta1,6' linkages, with beta1,4' linkages being more predominant. Beta1,4'- and beta 1,6'-galactosyl-lactose can be enriched or purified from these GOS mixtures as known in the art, for example by size exclusion chromatography. Other commercially available source of BGOS with predominantly beta1,4' and/or beta 1,6' linkages are Oligomate 55 and 50 from Yakult, and Cup Oligo form Nissin Sugar. Alternatively beta1,4'- and beta 1,6'-galactosyllactose are commercially available as single components (Carbosynth).

A suitable way to produce beta1,3' GOS, is by using a beta-galactosidase from *S. thermophilus*. Particularly suitable is the use of beta-galactosidase from strain CNCM I-1470 and/or CNCM I-1620 in a process as disclosed in example 4 of FR2723960 or example 6 of EP0778885. *S. thermophilus* CNCM I-1620 was deposited under the Budapest Treaty on 23 Aug. 1995 at Collection Nationale de Cultures de Microorganisms van Institute Pasteur, Paris, France by Compagnie Gervais Danone. Strain *S. thermophilus* CNCM I-1620 is also referred to as strain *S. thermophilus* ST065. *S. thermophilus* CNCM I-1470 was deposited under the Budapest Treaty on 25 Aug. 1994 at Collection Nationale de Cultures de Microorganisms van Institute Pasteur, Paris, France by Compagnie Gervais Danone. The composition of this GOS is also described in more detail in LeForestier et. al., 2009 Eur J Nutr, 48:457-464. Both strains have also been published in WO 96/06924. Another commercially available GOS rich in beta1,3 and beta1,6 galacto-oligosaccharides is Bimuno from Clasado, or Purimune from GTC Nutrition. Beta1,6'- and beta 1,3'-galactosyllactose can be enriched or purified from these GOS mixtures as known in the art, for example by size exclusion chromatography. Alternatively, pure beta1,3'-galactosyl-lactose is commercially available (Carbosynth).

The nutritional composition according to the present invention comprises preferably at least 200 mg GOS per 100 ml, more preferably at least 300 even more preferably at least 400 mg per 100 ml. Preferably the composition does not comprise more than 1500 mg of GOS per 100 ml, preferably not more than 1000 mg per 100 ml, more preferably not more than 800 mg per 100 ml. More preferably, the nutritional composition according to the present invention comprises GOS in an amount of 200 to 1500 mg/100 ml, even more preferably in an amount of 300 to 1000 mg/100 ml, even more preferably in an amount of 300 to 800 mg/100 ml.

Preferably the nutritional composition according to the present invention comprises at least 1.5 wt. % of GOS based on total dry weight of the composition, more preferably at least 2.2 wt. %, even more preferably at least 2.9 wt. %, all based on total dry weight of the composition. Preferably the composition does not comprise more than 10.9 wt. % of GOS based on total dry weight of the composition, more preferably not more than 7.3 wt. %, even more preferably not more than 5.8 wt. %. The nutritional composition according to the present invention preferably comprises GOS in an amount of 1.5 to 10.9 wt. %, more preferably in an amount of 2.2 to 7.3 wt. %, most preferably in an amount of 2.9 to 5.8 wt. %, all based on total dry weight of the nutritional composition.

Preferably the nutritional composition according to the present invention comprises at least 0.3 g GOS per 100 kcal, more preferably at least 0.5 g, even more preferably at least 0.6 g per 100 kcal. Preferably the composition does not comprise more than 2.3 g of GOS per 100 kcal, preferably not more than 1.5 g per 100 kcal, more preferably not more than 1.2 g per 100 kcal. More preferably, the nutritional composition according to the present invention comprises GOS in an amount of 0.3 to 2.3 g per 100 kcal, even more preferably in an amount of 0.5 to 1.5 g per 100 kcal, even more preferably in an amount of 0.6 to 1.2 g per 100 kcal.

Lower amounts result in a less effective composition, whereas the presence of higher amounts of GOS may result in side-effects such as osmotic disturbances, abdominal pain, bloating, gas formation and/or flatulence.

It is advantageous to have, besides the specific beta 1,3'-galactosyllactose (beta3'-GL), other galacto-oligosaccharides present in the present nutritional composition A mixture of GOS with different sizes and linkages will have an increased beneficial effect on the microbiota and an improved production of short chain fatty acids, which in its turn have a further improved beneficial effect on the intestinal barrier function. The presence of GOS other than beta3'-GL will in particular have an additional effect on the gut barrier function in the large intestine and end of the small intestine, whereas the beta3'-GL will be also, and most, effective in the small intestine.

In a preferred embodiment, the nutritional composition according to the present invention comprises 0.20 g to 1.5 g galacto-oligosaccharides per 100 ml, wherein 10 mg to 500 mg per 100 ml of the galacto-oligosaccharides is beta3'-GL. In another preferred embodiment, the nutritional composition according to the present invention comprises 0.20 g to 1.5 g galacto-oligosaccharides per 100 ml, wherein the amount of beta3'-GL is more than 20 wt. % based on total galacto-oligosaccharides. In another preferred embodiment, the nutritional composition according to the present invention comprises 1.5 wt. % to 10.9 wt. % g galacto-oligosaccharides based on total dry matter of the nutritional composition, wherein the amount of beta3'-GL is between 0.05 to 3.75 wt. % based on total dry matter of the nutritional composition. In another preferred embodiment, the nutritional composition according to the present invention comprises 1.5 wt. % to 10.9 wt. % g galacto-oligosaccharides based on total dry matter of the nutritional composition, wherein the amount beta3'-GL is more than 20 wt. % based on total galacto-oligosaccharides and wherein the amount of beta3'-GL is between 150 mg and 250 mg per 100 ml. In another preferred embodiment, the nutritional composition according to the present invention comprises 0.20 g to 1.5 g galacto-oligosaccharides per 100 ml, wherein the amount beta3'-GL is between 10 mg and 50 mg per 100 ml. Low doses of beta3'-GL can be used as it was found that beta3'-GL was already effective at a low dose in improving the gut barrier function.

The nutritional composition according to the present invention preferably comprises at least 10 mg beta3'-GL per 100 ml of the nutritional composition, more preferably 10 to 500 mg beta3'-GL, per 100 ml of the nutritional composition. In a preferred embodiment, the nutritional composition comprises 10 to 50 mg beta3'-GL, per 100 ml of the nutritional composition. In another preferred embodiment, the nutritional composition comprises 150 to 250 mg beta3'-GL, per 100 ml of the nutritional composition.

The nutritional composition according to the present invention preferably comprises 0.05 to 3.75 wt. %, more preferably 0.10 to 2.0 wt. % beta3'-GL, based on total dry weight of the nutritional composition. In a preferred embodiment, the nutritional composition comprises 0.05 to 0.375 wt. % beta3'-GL, based on total dry weight of the nutritional composition. In another preferred embodiment, the nutritional composition comprises 1.125 to 1.725 wt. % beta3'-GL, based on total dry weight of the nutritional composition.

The nutritional composition according to the present invention preferably comprises 15 to 750 mg beta3'-GL, per 100 kcal of the nutritional composition. In a preferred embodiment, the nutritional composition comprises 15 to 75 mg beta3'-GL per 100 kcal of the nutritional composition. In another preferred embodiment, the nutritional composition comprises 225 to 375 mg beta3'-GL per 100 kcal of the nutritional composition.

Preferably the composition comprises at least 1 wt. % of beta3'-GL based on total GOS. Preferably the nutritional composition comprises at most 70 wt. % beta3'-GL Glc based on total GOS. More preferably the nutritional composition comprises 1.3 to 10 wt. % beta3'-GL based on total GOS, most preferably 1.3 to 7 wt. % beta3'-GL based on total GOS. Preferably the composition comprises at least 0.8 wt. % of beta3'-GL based on total non-digestible oligosaccharides (NDO). Preferably the nutritional composition comprises at most 65 wt. % beta3'-GL based on total NDO. More preferably the nutritional composition comprises 1.1 to 9 wt. % beta3'-GL based on total NDO, most preferably 1.1 to 6.5 wt. % based on total NDO.

The nutritional composition according to the present invention may contain other non-digestible oligosaccharides next to galacto-oligosaccharides. Preferably the nutritional composition according to the present invention also comprises fructo-oligosaccharides (FOS), in particular long chain FOS, as described in more detail below.

The present nutritional composition preferably comprises 1.75 to 17.5 wt. % total non-digestible oligosaccharides, more preferably 2.8 to 10.5 wt. %, most preferably 4.2 to 7 wt. %, based on total dry weight of the nutritional composition. Based on 100 ml, the present nutritional composition preferably comprises 0.25 to 2.5 g total non-digestible oligosaccharides, more preferably 0.4 to 1.5 g, most preferably 0.6 to 1 g, based on 100 ml of the nutritional composition. A lower amount of non-digestible oligosaccharides will be less effective in improving the gut barrier function, whereas a too high amount will result in side-effects of bloating and abdominal discomfort. The total amount of non-digestible oligosaccharides includes galacto-oligosaccharides, including beta3'-GL, fructo-oligosaccharides and any additional non-digestible oligosaccharides that may further be present in the composition.

In a preferred embodiment, the nutritional composition according to the invention comprises:

- at least 45 wt. % oleic acid based on total fatty acids,
- no more than 10 wt. % palmitic acid based on total fatty acids, a wt/wt ratio of palmitic acid:oleic acid of no more than 1:4.5, and at least 0.05 wt. % beta1,3'-galactosyllactose based on total dry weight of the composition, and at least 1.5 wt. % galacto-oligosaccharides based on total dry weight of the composition, wherein the amount of galacto-oligosaccharides includes the amount of beta1,3'-galactosyllactose.

In a preferred embodiment, the nutritional composition according to the invention comprises:

3 to 10 wt. % palmitic acid based on total fatty acids, preferably 3 to 7 wt. %, 45 to 60 wt. % oleic acid based on total fatty acids, preferably 48 to 55 wt. %, a wt/wt ratio of palmitic acid:oleic acid in the range of 1:10 to 1:4.5, preferably in the range of 1:8 to 1:7, and at least 0.05 wt. % beta1,3'-galactosyllactose based on total dry weight of the composition, preferably at least 0.10 wt. % beta1,3'-galactosyllactose based on total dry weight of the composition.

In a further preferred embodiment, the nutritional composition according to the invention comprises:

3 to 10 wt. % palmitic acid based on total fatty acids, preferably 3 to 7 wt. %, 45 to 60 wt. % oleic acid based on total fatty acids, preferably 48 to 55 wt. %, a wt/wt ratio of palmitic acid:oleic acid in the range of 1:10 to 1:4.5, preferably in the range of 1:8 to 1:7, at least 0.05 wt. % beta1,3'-galactosyllactose based on total dry weight of the composition, preferably at least 0.10 wt. % beta1,3'-galactosyllactose based on total dry weight of the composition, and 1.5 wt. % to 10.9 wt. % galacto-oligosaccharides based on total dry weight of the composition, preferably 2.2 wt. % to 5.8 wt. % galacto-oligosaccharides based on total dry weight of the composition, wherein the amount of galacto-oligosaccharides includes the amount of beta1,3'-galactosyllactose.

Nutritional Composition

The nutritional composition according to the invention is not human milk. In other words, the nutritional composition according to the invention is a synthetic nutritional composition. The nutritional composition can also be named a formula, which by definition denotes that it concerns a non-naturally occurring nutritional composition.

The present composition is preferably enterally administered, more preferably orally.

The present nutritional composition is preferably an infant formula, a follow on formula or a young child formula. Examples of a young child formula are toddler milk, toddler formula and growing up milk. More preferably the nutritional composition is an infant formula or a follow on formula. The present nutritional composition can be advantageously applied as a complete nutrition for infants. An infant formula is defined as a formula for use in infants and can for example be a starter formula, intended for infants of 0 to 6 or 0 to 4 months of age. A follow on formula is intended for infants of 4 or 6 months to 12 months of age. At this age infants start weaning on other food. A young child formula, or toddler or growing up milk or formula is intended for children of 12 to 36 months of age. Preferably the present nutritional composition is an infant formula.

The present nutritional composition preferably comprises lipid, protein and carbohydrate and is preferably administered in liquid form. The present nutritional composition may also be in the form of a dry food, preferably in the form of a powder which is accompanied with instructions as to mix said dry food, preferably powder, with a suitable liquid, preferably water. The present nutritional composition may thus be in the form of a powder, suitable to reconstitute with water to provide a ready to drink nutritional composition, preferably a ready to drink infant formula, follow on formula or young child formula, more preferably a ready to drink infant formula or follow on formula. The nutritional composition according to the invention preferably comprises other fractions, such as vitamins, minerals, trace elements and other micronutrients in order to make it a complete nutritional composition. Preferably infant formulae comprise vitamins, minerals, trace elements and other micronutrients according to international directives.

The present nutritional composition preferably comprises lipid, protein and digestible carbohydrate wherein the lipid provides 25 to 65% of the total calories, the protein provides 6.5 to 16% of the total calories, and the digestible carbohydrate provides 20 to 80% of the total calories. Preferably, in the present nutritional composition the lipid provides 30 to 55% of the total calories, the protein provides 7 to 9% of the total calories, and the digestible carbohydrate provides 35 to 60% of the total calories. For calculation of the % of total calories for the protein, the total of energy provided by proteins, peptides and amino acids needs to be taken into account.

Preferably the lipid provides 3 to 7 g lipid per 100 kcal, preferably 3.5 to 6 g per 100 kcal, the protein provides 1.6 to 4 g per 100 kcal, preferably 1.7 to 2.3 g per 100 kcal and the digestible carbohydrate provides 5 to 20 g per 100 kcal, preferably 8 to 15 g per 100 kcal of the nutritional composition. Preferably the present nutritional composition comprises lipid providing 3.5 to 6 g per 100 kcal, protein providing 1.7 to 2.3 g per 100 kcal and digestible carbohydrate providing 8 to 15 g per 100 kcal of the nutritional composition.

Preferably the lipid provides 2.5 to 6.5 g lipid per 100 ml, preferably 2.5 to 4 g per 100 ml, the protein provides 1 to 3 g per 100 ml, preferably 1 to 1.5 g per 100 ml and the digestible carbohydrate provides 3 to 13 g per 100 ml, preferably 5 to 10 g per 100 ml of the nutritional composition. Preferably the present nutritional composition comprises lipid providing 2.0 to 6.5 g per 100 ml, protein providing 1 to 3 g per 100 ml and digestible carbohydrate providing 5 to 10 g per 100 ml of the nutritional composition.

Preferably the lipid provides 15 to 45 wt. %, preferably 20 to 30 wt. %, based on total dry weight of the composition, the protein provides 8 to 20 wt. %, preferably 8.5 to 11.5 wt. %, based on total dry weight of the composition and the digestible carbohydrates comprise 25 to 90 wt. %, preferably 40 to 75 wt. %, based on total dry weight of the composition. Preferably the present nutritional composition comprises lipid providing 20 to 30 wt. %, protein providing 8.5 to 11.5 wt. % and digestible carbohydrate providing 40 to 75 wt. %, all based on total dry weight of the composition.

The present nutritional composition preferably comprises protein. The protein used in the nutritional composition is preferably selected from the group consisting of non-human animal proteins, preferably milk proteins, vegetable proteins, such as preferably soy protein and/or rice protein, and mixtures thereof. The present nutritional composition preferably contains casein, and/or whey protein, more preferably bovine whey proteins and/or bovine casein. Thus in one embodiment the protein in the present nutritional composition comprises protein selected from the group consisting of whey protein and casein, preferably whey protein and casein, preferably the whey protein and/or casein is from cow's milk. The present nutritional composition preferably comprises casein and whey proteins in a weight ratio casein: whey protein of 10:90 to 90:10, more preferably 20:80 to 80:20, even more preferably 35:65 to 55:45.

The wt. % protein based on total dry weight of the present nutritional composition is calculated according to the Kjeldahl-method by measuring total nitrogen and using a conversion factor of 6.38 in case of casein, or a conversion factor of 6.25 for other proteins than casein. The term 'protein' or 'protein component' as used in the present invention refers to the sum of proteins, peptides and free amino acids.

The present nutritional composition preferably comprises protein providing 1.6 to 4.0 g protein per 100 kcal of the nutritional composition, preferably providing 11.7 to 2.3 g per 100 kcal of the nutritional composition. A too low protein content based on total calories will result in less adequate growth and development in infants and young children. A too high amount will put a metabolic burden, e.g. on the kidneys of infants and young children. When in liquid form, as a ready-to-feed liquid, the nutritional composition preferably comprises 1.0 to 3.0 g, more preferably 1.0 to 1.5 g protein per 100 ml. Based on total dry weight the present nutritional composition preferably comprises 8 to 20 wt. % protein, more preferably 8.5 to 11.5 wt. %, based on total dry weight of the total nutritional composition.

The present nutritional composition preferably comprises digestible carbohydrate providing 5 to 20 g per 100 kcal, preferably 8 to 15 g per 100 kcal. Preferably the amount of digestible carbohydrate in the present nutritional composition is 25 to 90 wt. %, more preferably 8.5 to 11.5 wt. %, based on total dry weight of the composition. Preferred digestible carbohydrates are lactose, glucose, sucrose, fructose, galactose, maltose, starch and maltodextrin. Lactose is the main digestible carbohydrate present in human milk. The present nutritional composition preferably comprises lactose. Preferably the present nutritional composition does not comprise high amounts of carbohydrates other than lactose. Compared to digestible carbohydrates such as maltodextrin, sucrose, glucose, maltose and other digestible carbohydrates with a high glycemic index, lactose has a lower glycemic index and is therefore preferred. The present nutritional composition preferably comprises digestible carbohydrate, wherein at least 35 wt. %, more preferably at least 50 wt. %, more preferably at least 60 wt. %, more preferably at least 75 wt. %, even more preferably at least 90 wt. %, most preferably at least 95 wt. % of the digestible carbohydrate is lactose. Based on total dry weight the present nutritional composition preferably comprises at least 25 wt. % lactose, preferably at least 40 wt. %, more preferably at least 50 wt. % lactose.

The nutritional composition preferably comprises non digestible oligosaccharides in the form of galacto-oligosaccharides. Beta1,3'-galactosyllactose is considered a non-digestible oligosaccharide, more in particular a non-digestible galacto-oligosaccharide. The beta 1,3'-galactosyllactose may be present in the nutritional composition according to the invention as such, or as part of a mixture of galacto-oligosaccharides (GOS), preferably beta-galacto-oligosaccharides (BGOS). In a preferred embodiment the beta 1,3'-galactosyllactose is present as part of a mixture of galacto-oligosaccharides. Galacto-oligosaccharides, and preferred embodiments of the present nutritional composition comprising galacto-oligosaccharides, are described in more detail above.

In one embodiment, the nutritional composition according to the invention comprises 1.6 to 4 g protein, 5 to 20 g digestible carbohydrates and 0.30 g to 2.3 g galacto-oligosaccharides per 100 kcal of the composition, wherein the amount of beta3'-GL is more than 20 wt. % based on total galacto-oligosaccharides. In another embodiment, the nutritional composition according to the invention comprises 1.6 to 4 g protein, 5 to 20 g digestible carbohydrates and 0.30 to 2.3 g galacto-oligosaccharides per 100 kcal of the composition, wherein the amount of beta3'-GL is between 150 mg and 250 mg per 100 ml. In yet another embodiment, the nutritional composition according to the invention comprises 1.6 to 4 g protein, 5 to 20 g digestible carbohydrates and 0.30 g to 2.3 g galacto-oligosaccharides per 100 kcal of the composition, wherein the amount of beta3'-GL is more than 20 wt. % based on total galacto-oligosaccharides, and wherein the amount of beta3'-GL is between 150 mg and 250 mg per 100 ml.

In another embodiment, the nutritional composition according to the invention comprises 1.6 to 4 g protein, 5 to 20 g digestible carbohydrates and 0.30 g to 2.3 g galacto-oligosaccharides per 100 kcal of the composition, wherein the amount of beta3'-GL is between 10 mg and 50 mg per 100 ml.

Preferably the present nutritional composition also comprises fructo-oligosaccharides (FOS). The term fructo-oligosaccharides as used in the present invention refers to carbohydrates composed of over 50%, preferably over 65% fructose units based on monomeric subunits, in which at least 50%, more preferably at least 75%, even more preferably at least 90%, of the fructose units are linked together via a beta-glycosidic linkage, preferably a beta-2,1 glycosidic linkage. A glucose unit may be present at the reducing end of the chain of fructose units. Preferably the fructo-oligosaccharides have a DP or average DP in the range of 2 to 250, more preferably 2 to 100, even more preferably 10 to 60. The term fructo-oligosaccharides comprises levan, hydrolysed levan, inulin, hydrolysed inulin, and synthesised fructo-oligosaccharides. Preferably the preparation comprises long chain fructo-oligosaccharides with an average DP above 20. Fructo-oligosaccharide suitable for use in the composition of the invention is also readily commercially available, e.g. RaftilineHP (Orafti). Preferably the nutritional composition according to the present invention comprises at least 25 mg FOS per 100 ml, more preferably at least 40 even more preferably at least 60 mg. Preferably the composition does not comprise more than 250 mg FOS per 100 ml, more preferably not more than 150 mg per 100 ml and most preferably not more than 100 mg per 100 ml. The amount of FOS is preferably 25 to 250 mg fructo-oligosaccharides per 100 ml, preferably 40 to 150 mg per 100 ml, more preferably 60 to 100 mg per 100 ml. Preferably the nutritional composition according to the present invention comprises at least 0.15 wt. % FOS based on total dry weight, more preferably at least 0.25 wt. %, even more preferably at least 0.4 wt. %. Preferably the composition does not comprise more than 1.5 wt. % FOS based on total dry weight of the composition, more preferably not more than 1.0 wt. %. The presence of FOS shows a further improved effect on the microbiota and its SCFA production when combined with the galacto-oligosaccharides. This then has an improved effect on the gut barrier function.

Preferably the present nutritional composition comprises a mixture of galacto-oligosaccharides (including the beta 1,3'-galactosyllactose) and fructo-oligosaccharides. Preferably the mixture of galacto-oligosaccharides and fructo-oligosaccharides is present in a weight ratio of from 1/99 to 99/1, more preferably from 1/19 to 19/1, more preferably from 1/1 to 19/1, more preferably from 2/1 to 15/1, more preferably from 5/1 to 12/1, even more preferably from 8/1 to 10/1, even more preferably in a ratio of about 9/1. This weight ratio is particularly advantageous when the galacto-oligosaccharides have a low average DP and fructo-oligosaccharides has a relatively high DP. Most preferred is a mixture of galacto-oligosaccharides with an average DP below 10, preferably below 6, and fructo-oligosaccharides with an average DP above 7, preferably above 11, even more preferably above 20.

It is also important that the nutritional composition according to the present invention does not have an excessive caloric density, however still provides sufficient calories to feed the subject. Hence, the liquid food preferably has a caloric density between 0.1 and 2.5 kcal/ml, more preferably a caloric density of between 0.5 and 1.5 kcal/ml, even more preferably between 0.6 and 0.8 kcal/ml, and most preferably between 0.65 and 0.7 kcal/ml.

The nutritional composition, preferably an infant formula, follow on formula or young child formula, according to the invention is for use in providing nutrition to an infant or young child, preferably an infant.

Application

It was surprisingly found that a high level of oleic acid has a positive effect on the gut barrier function. To the contrary, palmitic acid does not provide such effect. Moreover this effect of oleic acid was further improved in combination with SCFA's; this improvement was beyond the individual contribution of oleic acid and SCFA's. SCFA's are formed in the large intestine upon fermentation of non-digestible carbohydrates such as GOS or GOS combined with FOS. Therefore the combination of a composition with a high level of oleic acid and GOS has a particular good effect on gut barrier function. It was further demonstrated that more acetate and lactate is formed and a larger pH drop is observed upon fermentation of beta1,3'-galactosyllactose compared to other GOS. Moreover it was demonstrated that beta1,3'-galactosyllactose provides improved protection against intestinal barrier disruption and prevention against permeability increase compared to other GOS. Moreover it was found that found that in particular the combination of beta1,3'-galactosyllactose with oleic acid showed a surprising synergistic effect on protecting the intestinal epithelial barrier function. This effect was specific for the combination with oleic acid as it was not observed with palmitic acid. Therefore the combination of a composition with a high level of oleic acid and comprising beta1,3'-galactosyllactose has a particular good effect on gut barrier function. More in particular, the combination of a composition with a high level of oleic acid and comprising GOS and beta1,3'-galactosyllactose has a particular good effect on gut barrier function. Considering it was found that palmitic acid provides no positive effect on the gut barrier function and considering that a lipid composition high in one fatty acid necessarily needs fatty acids that in low amounts present, it was found to be advantageous to limit the maximum amount of palmitic acid to a relatively low level. This limitation goes against common knowledge for infant formula, follow-on formula and young child formula considering human milk comprises a high level of palmitic acid and as human milk is the golden standard for such formula the skilled person strives for a high level of palmitic acid in infant formula, follow-on formula and young child formula.

The present invention thus relates to a nutritional composition comprising:

- at least 45 wt. % oleic acid based on total fatty acids,
- no more than 10 wt. % palmitic acid based on total fatty acids,
- a wt/wt ratio of palmitic acid:oleic acid of no more than 1:4.5, and
- at least 0.05 wt. % beta1,3'-galactosyllactose based on total dry weight of the composition, for use in improving intestinal barrier function.

The invention can also be worded as the use of oleic acid, palmitic acid and beta1,3'-galactosyllactose for the manufacture of a nutritional composition for use in improving intestinal barrier function, wherein the nutritional composition comprises

- at least 45 wt. % oleic acid based on total fatty acids,
- no more than 10 wt. % palmitic acid based on total fatty acids,
- a wt/wt ratio of palmitic acid:oleic acid of no more than 1:4.5, and
- at least 0.05 wt. % beta1,3'-galactosyllactose based on total dry weight of the composition.

In other words the invention relates to a method for increasing intestinal barrier function in a subject, comprising administering to the subject a nutritional composition comprising:

- at least 45 wt. % oleic acid based on total fatty acids,
- no more than 10 wt. % palmitic acid based on total fatty acids,
- a wt/wt ratio of palmitic acid:oleic acid of no more than 1:4.5, and
- at least 0.05 wt. % beta1,3'-galactosyllactose based on total dry weight of the composition.

In case improving intestinal barrier function is considered non-therapeutic, the present invention can be worded as a non-therapeutic method for improving intestinal barrier function in a subject, comprising administering to the subject a nutritional composition comprising:

- at least 45 wt. % oleic acid based on total fatty acids,
- no more than 10 wt. % palmitic acid based on total fatty acids,
- a wt/wt ratio of palmitic acid:oleic acid of no more than 1:4.5, and
- at least 0.05 wt. % beta1,3'-galactosyllactose based on total dry weight of the composition.

In one embodiment the present invention relates to a nutritional composition comprising:

- at least 45 wt. % oleic acid based on total fatty acids,
- no more than 10 wt. % palmitic acid based on total fatty acids,
- a wt/wt ratio of palmitic acid:oleic acid of no more than 1:4.5,
- at least 0.05 wt. % beta1,3'-galactosyllactose based on total dry weight of the composition, and
- at least 1.5 wt. % galacto-oligosaccharides based on total dry weight of the composition, wherein the amount of galacto-oligosaccharides includes the amount of beta1,3'-galactosyllactose, for use in improving intestinal barrier function.

This embodiment can also be worded as the use of oleic acid, palmitic acid and galacto-oligosaccharides for the manufacture of a nutritional composition for use in improving intestinal barrier function, wherein the nutritional composition comprises

- at least 45 wt. % oleic acid based on total fatty acids,
- no more than 10 wt. % palmitic acid based on total fatty acids,
- a wt/wt ratio of palmitic acid:oleic acid of no more than 1:4.5, and
- at least 0.05 wt. % beta1,3'-galactosyllactose based on total dry weight of the composition, and at least 1.5 wt. % galacto-oligosaccharides based on total dry weight of the composition, wherein the amount of galacto-oligosaccharides includes the amount of beta1,3'-galactosyllactose.

In other words the invention relates to a method for increasing intestinal barrier function in a subject, comprising administering to the subject a nutritional composition comprising:

at least 45 wt. % oleic acid based on total fatty acids,
no more than 10 wt. % palmitic acid based on total fatty acids,
a wt/wt ratio of palmitic acid:oleic acid of no more than 1:4.5,
at least 0.05 wt. % beta1,3'-galactosyllactose based on total dry weight of the composition, and
at least 1.5 wt. % galacto-oligosaccharides based on total dry weight of the composition, wherein the amount of galacto-oligosaccharides includes the amount of beta1,3'-galactosyllactose.

In case improving intestinal barrier function is considered non-therapeutic, the present invention can be worded as a non-therapeutic method for improving intestinal barrier function in a subject, comprising administering to the subject a nutritional composition comprising:

at least 45 wt. % oleic acid based on total fatty acids,
no more than 10 wt. % palmitic acid based on total fatty acids,
a wt/wt ratio of palmitic acid:oleic acid of no more than 1:4.5,
at least 0.05 wt. % beta1,3'-galactosyllactose based on total dry weight of the composition, and
at least 1.5 wt. % galacto-oligosaccharides based on total dry weight of the composition, wherein the amount of galacto-oligosaccharides includes the amount of beta1,3'-galactosyllactose.

Furthermore the invention also concerns the above nutritional compositions for use in the prevention and/or treatment of intestinal barrier disruption in a subject, a method for prevention and/or treatment of intestinal barrier disruption in a subject comprising administering the above nutritional composition to a subject, and/or a non-therapeutic method for prevention and/or treatment of intestinal barrier disruption in a subject comprising administering the above nutritional composition to a subject.

The invention further relates to a nutritional composition comprising:

at least 45 wt. % oleic acid based on total fatty acids,
no more than 10 wt. % palmitic acid based on total fatty acids,
a wt/wt ratio of palmitic acid:oleic acid of no more than 1:4.5, and
at least 0.05 wt. % beta1,3'-galactosyllactose based on total dry weight of the composition, for use in treating and/or preventing intestinal barrier mediated disorders selected from the group consisting of intestinal inflammation, infections originating from the intestine and food allergy.

The invention can also be worded as the use of oleic acid, palmitic acid and beta1,3'-galactosyllactose for the manufacture of a nutritional composition for use in treating and/or preventing intestinal barrier mediated disorders selected from the group consisting of intestinal inflammation, infections originating from the intestine and food allergy, wherein the nutritional composition comprises at least 45 wt. % oleic acid based on total fatty acids,
no more than 10 wt. % palmitic acid based on total fatty acids,
a wt/wt ratio of palmitic acid:oleic acid of no more than 1:4.5, and
at least 0.05 wt. % beta1,3'-galactosyllactose based on total dry weight of the composition.

In other words the invention relates to a method for treating and/or preventing intestinal barrier mediated disorders selected from the group consisting of intestinal inflammation, infections originating from the intestine and food allergy in a subject, comprising administering to the subject a nutritional composition comprising:

at least 45 wt. % oleic acid based on total fatty acids,
no more than 10 wt. % palmitic acid based on total fatty acids,
a wt/wt ratio of palmitic acid:oleic acid of no more than 1:4.5, and
at least 0.05 wt. % beta1,3'-galactosyllactose based on total dry weight of the composition.

The invention further relates to a nutritional composition comprising:

at least 45 wt. % oleic acid based on total fatty acids,
no more than 10 wt. % palmitic acid based on total fatty acids,
a wt/wt ratio of palmitic acid:oleic acid of no more than 1:4.5,
at least 0.05 wt. % beta1,3'-galactosyllactose based on total dry weight of the composition, and
at least 1.5 wt. % galacto-oligosaccharides based on total dry weight of the composition, wherein the amount of galacto-oligosaccharides includes the amount of beta1,3'-galactosyllactose, for use in treating and/or preventing intestinal barrier mediated disorders selected from the group consisting of intestinal inflammation, infections originating from the intestine and food allergy.

This embodiment can also be worded as the use of oleic acid, palmitic acid and galacto-oligosaccharides for the manufacture of a nutritional composition for use in treating and/or preventing intestinal barrier mediated disorders selected from the group consisting of intestinal inflammation, infections originating from the intestine and food allergy, wherein the nutritional composition comprises at least 45 wt. % oleic acid based on total fatty acids,
no more than 10 wt. % palmitic acid based on total fatty acids,
a wt/wt ratio of palmitic acid:oleic acid of no more than 1:4.5, and
at least 0.05 wt. % beta1,3'-galactosyllactose based on total dry weight of the composition, and
at least 1.5 wt. % galacto-oligosaccharides based on total dry weight of the composition, wherein the amount of galacto-oligosaccharides includes the amount of beta1,3'-galactosyllactose In other words the invention relates to a method for treating and/or preventing intestinal barrier mediated disorders selected from the group consisting of intestinal inflammation, infections originating from the intestine and food allergy in a subject, comprising administering to the subject a nutritional composition comprising:

at least 45 wt. % oleic acid based on total fatty acids,
no more than 10 wt. % palmitic acid based on total fatty acids,
a wt/wt ratio of palmitic acid:oleic acid of no more than 1:4.5,
at least 0.05 wt. % beta1,3'-galactosyllactose based on total dry weight of the composition, and at least 1.5 wt. % galacto-oligosaccharides based on total dry weight of the composition, wherein the amount of galacto-oligosaccharides includes the amount of beta1, 3'-galactosyllactose.

In the context of the present invention the term "prevention" means "reducing the risk of" or "reducing the severity of". The term "prevention of a certain condition" also includes "treatment of a person at risk of said condition".

The methods or uses according to the present invention, comprising administering the present nutritional composition to a subject in need thereof, also refer to administering an effective amount of the nutritional composition to the subject.

In a preferred embodiment, the nutritional composition according to the invention is an infant formula, follow on formula or young child formula, preferably an infant formula. In the context of the present invention, an infant is defined as a human having an age of 0 to 12 months and a young child is defined as a human having an age of 13 to 36 months. The present nutritional composition is thus preferably administered to an infant or young child, more preferably to an infant with an age of 0 to 12 months, most preferably an infant with an age of 0 to 6 months. In a preferred embodiment, the methods or uses according to the present invention are for healthy infants, preferably for healthy, term infants. In newborns, the intestinal tract is not yet fully developed and infants are in need of support for developing the intestinal barrier function and/or resistance to pathogens and/or allergens. In one embodiment infants born via c-section are in need of the support on intestinal barrier resistance and/or function according to the present invention.

In a preferred embodiment, the subject in the present invention is a subject having an impaired intestinal barrier or is at risk of developing an impaired intestinal barrier. In one embodiment the subject is a preterm or prematurely born infant. Especially this subgroup of infants may benefit from being administered the nutritional composition of the invention, since organs making up the intestinal tract of preterms are immature, as opposed to term-born infants and thus in need of increasing the intestinal barrier function, improved intestinal barrier integrity, reduced permeability of the intestinal barrier and/or reduced intestinal barrier disruption.

In infants, intestinal barrier function can easily be determined without the need for invasive techniques, for example by a mannitol-lactulose absorption test, see Jalonen, J Allergy Clin Immunol 1991; 88:737-742.

Intestinal epithelial stress or damage may contribute to allergic sensitization against certain food antigens. Bol-Schoenmakers et al. (Mucosal Immunol. 2016 November; 9(6):1477-1486) demonstrated that deoxynivalenol (DON) facilitates allergic sensitization to food proteins and that development of sensitization can be induced by different molecular mechanisms and local immune responses (IL-8). Therefore, it is assumed that food contaminants, including DON, contribute to allergic sensitization in humans.

Mycotoxins can appear in the food chain as a result of fungal infection of plant products (e.g., forage, grain, plant protein, processed grain by-products, roughage and molasses products), and can either be eaten directly by humans, or introduced by contaminated grains, livestock or other animal feedstuff(s). Since DON frequently occurs in toxicologically relevant concentrations in cereals and grains, it can be qualified as a genuine problem for all humans and animals consuming a diet comprising cereals and/or grains. It is a particular concern for infants, and with that in mind Codex Committees on Contaminants in Food (CCCF) have been dedicated to provide maximum limits for deoxynivalenol levels still deemed acceptable in raw cereal grains such as wheat and barley grain and infant formula.

In an embodiment of the present invention, the nutritional composition for use, or the nutritional composition in the methods and uses according to the invention is administered to subjects at risk, preferably infants or young children that consume cereals or cereal-comprising products, in particular on two days or more per week, for example on three days or four days or five days or six days per week or daily, and/or infants or young children that suffer from or are at increased risk of suffering from food allergy and/or atopic dermatitis. An infant at increased risk of suffering from or developing a food allergy is an infant born from parents of whom one or both suffers from an atopic disease, or an infant who has one or more siblings suffering from an atopic disease. These infants and young children have a higher risk of becoming allergic to certain foods, e.g. to dietary proteins, in particular cow's milk proteins.

EXAMPLES

Example 1: Gut Barrier Effect of Oleic Acid, Palmitic Acid and Short Chain Fatty Acids The effect of palmitic acid and oleic acid combined with a mixture of short chain fatty acids (SCFA mix) having a concentration profile that is typical for fermentation of a mixture of galacto-oligosaccharides (GOS) derived from VivinalGOS and long chain fructo-oligosaccharides (RaftilineHP) in a ratio of 9/1 (w/w) on barrier permeability was investigated. The concentration profiles of SCFA is as disclosed in Example 3 of EP2100520 (incorporated by reference herein), specifically as shown in FIG. 3A of EP2100520 (incorporated by reference herein) (see second bar in FIG. 3A), i.e. about 75% being acetic acid. Oleic acid and palmitic acid were obtained from Sigma-Aldrich and coupled to fatty acid free Bovine Serum Albumin (BSA, Sigma-Aldrich) prior to cell treatment.

Methods

T84 human intestinal epithelial cells are commonly used to study intestinal barrier integrity in vitro. T84 cells (ATCC, USA) were cultured on 12 mm transwell inserts (0.4 m, Corning Costrar, USA) in DMEM-F12 glutamax with penicillin-streptomycin (100 IU/ml), supplemented with 10% FBS-HI. T84 cells were used 14 days after reaching confluence. Monolayers of T84 cultured on transwell filters were pre-incubated with fatty acids, SCFA mix or a combination thereof for a period of 24 hours.

Epithelial barrier integrity was assessed by measuring transepithelial resistance (TEER; $\Omega \times cm^2$) with the epithelial volt-ohm meter (Millicell ERS-2; Millipore USA). TEER measurements were performed at 0, 24, h of incubation. TEER values of the fatty acids (i.e. SCFA, OA, PA) are expressed relative to the medium control TEER values at 24 h. Results are shown in Table 1.

TABLE 1

Effect of LC-PUFA on the gut barrier function.

| Fatty acid | Conc LC-PUFA (μM) | SCFA mix (mM) (C2-C4 fatty acids) | % TEER (24 h) |
|---|---|---|---|
| — | — | — | 100 |
| — | 0 | 40 | 160 |
| OA | 50 | 0 | 134 |
| OA | 50 | 40 | 210 |
| Theoretical value OA + SCFA | | | 194 |
| PA | 50 | 0 | 94 |
| PA | 50 | 40 | 143 |
| Theoretical value PA + SCFA | | | 154 |

This example shows that palmitic acid alone has a negative effect of −6% on the gut barrier function. SCFA improves the gut barrier function by 60%. The combination of palmitic acid and short chain fatty acids shows a lower gut barrier function of 43% increase. An additive effect would have resulted in a 54% increase. Oleic acid improves the gut barrier function with 34%. In combination with SCFA the barrier function highly increased with 110%. An additive effect is would have resulted in a 94% increase.

The improved effect on the gut barrier function of oleic acid compared to palmitic acid (34% increase vs 6% decrease) was further enhanced when SCFA were present (a 110% increase vs a 60% increase). Therefore, this example is indicative of an improved effect on the intestinal barrier function in a composition high in oleic acid, when combining with galacto-oligosaccharides that can be fermented to short chain fatty acids. In addition, the example is indicative that a low level of palmitic acid contributes to the improved effect on the intestinal barrier function.

Example 2: Fermentation of 3'-GL, 4'-GL or 6'-GL by Intestinal Microbiota

The effect of pure 3'-GL, 4'-GL, and 6'-GL of the three galactosyllactoses functionality (pH, lactate, acetate levels) was evaluated. Beta1,3-galactosyllactose (beat3'-GL), beta 1,4-galactosyllactose (beta4'-GL) and beta 1,6-galactosyllactose (beta6'-GL) were obtained from Carbosynth (Berkshire, UK) Measurements of all parameters were performed after a 24-hour incubation in the high-throughput anaerobic colon model, i-screen™ (TNO, Zeist, the Netherlands).

Fecal samples from 3 healthy infants (aged 1-4 months) were pooled and activated for 4 hours in a modified standard ileal efflux medium (pH 6.0) at 37° C. under anaerobic conditions. Next, each GL was added. After an incubation for 24 hours at 37° C. under anaerobic conditions, samples were collected for further analysis and pH levels were immediately measured using a pH meter MultiCal pH 526 (WTW, Weilheim, Germany). The samples were centrifuged at 4,000 g for 5 minutes and the supernatant was filter sterilized using 0.45 μm filters. For the SCFA analysis, a mixture of formic acid (20%), methanol and 2-ethyl butyric acid (internal standard, 2 mg/ml in methanol) was added to the filtered supernatant. A 3 μl sample with a split ratio of 75.0 was injected on a GC-column (ZB-5HT inferno, ID 0.52 mm, film thickness 0.10 um; Zebron; phenomenex, USA) in a Shimadzu GC-2014 gas chromatograph. The levels of acetic acid and lactic acid were measured. For lactate analysis, the total of D- and L-lactate was determined the filtered supernatant by the Arena 20XL analyser. This assay is based on the D- and L-lactic acid assay kits (Thermo Fisher Scientific oy, www.e-labeling.eu/TSF9843061FIJ and www.e-labeling.eu/TSF9843081 FU). The assay was performed following the manufacturer's instructions with one adaptation: the reagents DLac RI and LLac RI from the two kits were mixed in a 1:1 ratio to detect both L and D isomers of lactic acid simultaneously. Calibration of the assay was done with an 'Acid combination standard' (order number 984382) containing both L-lactic acid and D-lactic acid.

For all three GLs a decrease in pH was observed and an increase was observed for acetate and lactate. 3'-GL showed the highest levels of acetate and lactate and the lowest pH level.

TABLE 2 pH reduction and organic acid formation at t = 24 h upon fermentation of 3 different galactosyllactoses by infant microbiota.

| | | pH | acetate | lactate |
|---|---|---|---|---|
| Blanc | | 6.1 | 34.2 | 0.0 |
| beta3'-GL | 3 mg/ml | 5.5 | 61.3 | 0.0 |
| | 9 mg/ml | 4.5 | 77.1 | 1.3 |
| beta4'-GL | 3 mg/ml | 5.6 | 52.2 | 0.0 |
| | 9 mg/ml | 4.7 | 65.4 | 3.6 |
| beta6'-GL | 3 mg/ml | 5.6 | 51.9 | 0.0 |
| | 9 mg/ml | 4.9 | 74.3 | 2.7 |

Example 3: Beta1,3'-Galactosyllactose Specifically Protects Against Intestinal Barrier Disruption and Prevents Permeability Increase beta 1,3'-galactosyl-lactose (beta3'-GL), beta1,4'-galactosyllactose (beta4'-GL) and beta1,6'-galactosyl-lactose (beta6'-GL) were obtained from Carbosynth (Berkshire, UK). alpha1,3'-galactosyl-lactose (alpha3'-GL) was obtained from Elicityl (Crolles, France). Purified deoxydivalenol (DON) (D0156; Sigma Aldrich, St Luis, MO, USA) was dissolved in pure ethanol and stored at −20° C. Human epithelial colorectal adenocarcinoma (Caco-2) cells were obtained from American Type Tissue Collection (Code HTB-37) (Manasse, VA, USA, passage 90-102).

Caco-2 cells were used according to established methods. In brief: cells were cultured in Dulbecco's modified Eagle medium (DMEM) and seeded at a density of $0.3\times10^5$ cells into 0.3 $cm^2$ high pore density (0.4 μm) inserts with a polyethylene terephthalate membrane (BD Biosciences, Franklin Lakes, NJ, USA) placed in a 24-well plate. The Caco-2 cells were maintained in a humidified atmosphere of 95% air and 5% $CO_2$ at 37° C. After 17-19 days of culturing, a confluent monolayer was obtained with a mean Transepithelial electrical resistance (TEER) exceeding 400 $\Omega cm^2$ measured by a Millicell-Electrical Resistance System voltohm-meter (Millipore, Temecula, CA, USA).

Caco-2 cell monolayers were thus grown in a transwell system, which is a model for intestinal barrier function. The monolayers were pretreated for 24 h with different GLs, including beta3'-GL, alpha3'-GL, beta4'-GL and beta6'-GL in a concentration of 0.75 wt. % of the GL, before being exposed to the fungal toxin deoxynivalenol (DON), which is a trigger and model compound to impair intestinal barrier. DON was diluted to a final concentration of 4.2 μM in complete cell medium and added to the apical side as well as to the basolateral side of the transwell inserts. This DON concentration did not affect the viability of the Caco-2 cells. Incubation with DON was 24 h.

Measurements of the transepithelial electrical resistance (TEER) and lucifer yellow (LY) permeability were conducted to investigate barrier integrity. For TEER measurements a Millicel-ERS voltohmmeter connected to a pair of chopsticks electrodes was used to measure the TEER values. Results are expressed as a percentage of the initial value. For paracellular tracer flux assay the membrane impermeable lucifer yellow (LY) (Sigma, St Luis, MO, USA) was added in a concentration of 16 μg/ml to the apical compartment in the transwell plate for 4 h, and the paracellular flux was determined by measuring the fluorescence intensity in the basolateral compartment with a spectrophotofluorometer (FLUOstar Optima, BMG Labtech, Offenburg, Germany) set at excitation and emission wavelengths of 410 and 520 nm, respectively. Release of interleukin-8 (IL-8 or CXCL8), which is a typical marker for inflammation, was quantified in the medium of the apical side and the basolateral side of the Caco-2 transwell inserts in response to the treatments. CXCL8 concentrations were measured by using the human IL-8 ELISA assay (BD Biosciences, Pharmingem, San Diego, CA, USA) according to manufacturer's instructions. For more details on materials and methods see Akbari et al, 2016, Eur J Nutr. 56(5):1919-1930.

Figure 2:
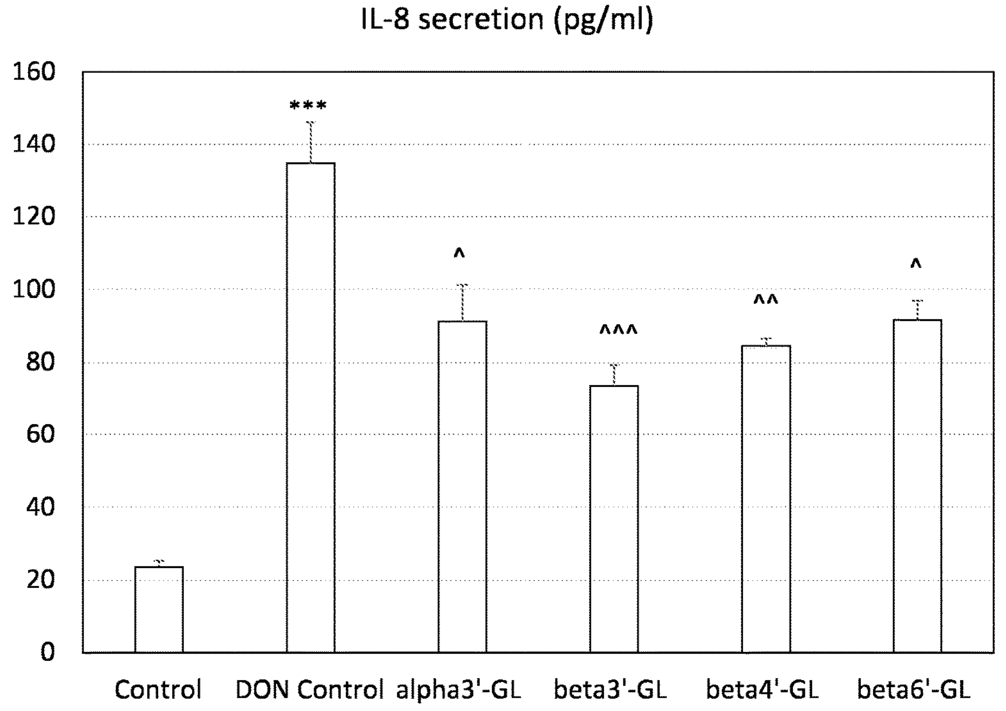
FIG. 2: Effects of different galactosyllactoses (GLs) on the DON-induced release of IL-8. For both

The results are shown in FIG. 1 A, B, C and D and in FIG. 2.

As can be seen from FIGS. 1A-D, the presence of DON disrupted the barrier function as shown by a decreased TEER value and an increased LY flux for the DON-control samples. Additionally, the presence of DON increased CXCL8 (IL-8) release, as shown in FIG. 2. FIGS. 1A-D further show that the presence of beta3'-GL prevented the DON-induced loss of epithelial barrier integrity as measured by increased TEER values and a reduction in the DON-affected LY flux across the intestinal epithelial monolayer. beta4'-GL and beta6'-GL did not show a significant effect on the intestinal epithelial barrier function. Interestingly, beta3'-GL, i.e. the galactosyl-lactose with a beta1-3 glycosidic linkage, was effective in protecting the intestinal barrier function, whereas alpha3'-GL, i.e. the galactosyl-lactose with an alpha1-3 glycosidic linkage, did not prevent the DON-induced disrupted intestinal barrier. In contrast, all galactosyl-lactoses were able to decrease the DON-induced IL-8 release, as is shown in FIG. 2.

These results are indicative for the specific effect of beta3'-GL (herein also referred to as beta1,3'-galactosyllactose or Gal (beta 1-3)-Gal (beta 1-4)-Glc) on protecting the intestinal epithelial barrier function, in particular under conditions of challenges, which goes beyond and/or is independent of an effect on preventing an inflammatory response, and/or of an effect on or via the microbiota. These results are thus indicative of an effect that beta3'-GL has on increasing the intestinal barrier function and/or on the prevention and/or treatment of intestinal barrier disruption.

Example 4: Also in Mixtures of Galacto-Oligosaccharides Beta3'-GL Specifically Protects Against Intestinal Barrier Disruption and Prevents Permeability Increase Several GOS preparations, comprising varying amounts of beta3'-GL, were tested in this experiment. As a source of beta4'-GL and beta6'-GL VivinalGOS (VGOS) was used. VivinalGOS is available from FrieslandCampina Domo (Amersfoort, The Netherlands) and contains about 59% GOS on dry matter. The DP3 of this GOS is predominantly 4'GL and 6'G.

Another GOS preparation, herein referred to as TOS, was produced in house by incubating a lactose mixture with *Streptococcus thermophilus* strain ST065 (this strain is also referred to as strain *S. thermophilus* CNCM I-1620), as described in more detail in WO 96/06924, FR2723960 and EP0778885, and in LeForestier et. al., 2009 Eur J Nutr, 48:457-464, with the additional step that *S. thermophilus* cell debris material was removed by centrifugation. The obtained TOS was used as a source of beta4'-GL, beta6'-GL and beta3'-GL. The amount of galacto-oligosaccharides (excluding lactose, galactose and glucose) was 10.2 wt. % per 100 ml, of which about 60-65 wt. % (62 wt. %) was beta3'-GL, the remainder being 6'-GL and non-digestible oligosaccharides with DP 2, 4 and 5 (see also WO 96/06924, FR2723960 and EP0778885 and LeForestier et. al., 2009 Eur J Nutr, 48:457-464).

Barrier function experiments were performed in a similar way as in example 3 using the following concentrations of Vivinal GOS (VGOS): 0 (Control), 0.25 wt. % (VGOS 0.25), 0.5 wt. % (VGOS 0.5), 0.75 wt. % (VGOS 0.75), 1 wt. % (VGOS 1), 1.5 wt. % (VGOS 1.5) and 2 wt. % (VGOS 2). For TOS concentrations of 0.25 wt. % (TOS 0.25) and 0.5 wt. % (TOS 0.5) were tested. The results are shown in Tables 3 and 4.

The effects of different GOS mixtures on the DON-induced impairment of the Caco-2 cell monolayer integrity were measured. Different GLs were tested for transepithelial electrical resistance (TEER), as shown in Table 2, and for the translocation of lucifer yellow (LYF) to the basolateral compartment, as shown in Table 3. TEER was expressed as a percentage of the initial value and LYF was expressed in ng/cm$^2$xh. GOS is VivinalGOS. TOS is the galacto-oligosaccharide mixture produced by *S. thermophilus* ST065 beta galactosidase and containing about 65 wt. % beta3'-GL based on total galacto-oligosaccharides. Data in Tables 2 and 3 are the mean±s.e. *: p<0.05 compared to control, : p<0.01 compared to control; *: p<0.001 compared to control; ^: p<0.05 compared to DON control; ^^ p<0.01 compared to DON Control; ^^^ p<0.001 compared to DON Control.

TABLE 3

Transepithelial electrical resistance (TEER) for different GOS mixtures, wherein TEER is expressed as a percentage of the initial value.

| TEER | Control | DON | VGOS 0.25 | VGOS 0.5 | VGOS 0.75 | VGOS 1 | VGOS 1.5 | VGOS 2 | TOS 0.25 | TOS 0.5 |
|---|---|---|---|---|---|---|---|---|---|---|
| Mean | 99.95 | 29.93*** | 33.04*** | 34.75*** | 34.83*** | 36.36*** | 47.5*** | 90.66^^ | 88.9^^^^ | 85.84^^ |
| Std. Error | 2.488 | 0.0353 | 1.632 | 0.4837 | 2.387 | 3.595 | 0.3964 | 2.144 | 7.025 | 4.165 |

TABLE 4

Translocation of lucifer yellow (LYF) to the basolateral compartment for different GOS mixtures, wherein LYF is expressed in ng/cm$^2$xh.

| LYF | Control | DON | VGOS 0.25 | VGOS 0.5 | VGOS 0.75 | VGOS 1 | VGOS 1.5 | VGOS 2 | TOS 0.25 | TOS 0.5 |
|---|---|---|---|---|---|---|---|---|---|---|
| Mean | 377.8 | 622.8*** | 618.9^*** | 571.9*** | 574.8*** | 451.1** ^^ | 396.3^^^ | 384.9^^^ | 406.8^^^ | 436^^^ |
| Std. Error | 1.208 | 25.31 | 13.05 | 9.299 | 6.053 | 1.598 | 10.31 | 4.166 | 4.456 | 1.975 |

VGOS only improved the barrier function as determined by preventing TEER decrease at relatively high concentration of 2 wt. %. Also the LY flux was only prevented by relatively high concentrations of VGOS of 1 wt. % or above. TOS, on the other hand, was already effective at a concentration of 0.25 wt. %. Since the main difference between VGOS and TOS is the presence of GOS with a beta1.3' link between the galactose moieties in TOS, and more in particular the presence of a high amount of beta3'-GL in TOS, this is indicative again for an effect of beta3'-GL on the gut barrier function, and this effect is maintained in the presence of other GOS structures. Also this effect is observed with beta3'-GL concentrations lower than about 0.17 wt. %.

Example 5: a Combination of Oleic Acid and Beta1.3'-Galactosyllactose Synergistically Protects Against Intestinal Barrier Disruption, Whereas a Combination of Palmitic Acid and Beta1,3'-Galactosyllactose does not Barrier function experiments were performed using the method as described in example 3. Oleic acid (OA) and palmitic acid were obtained from Sigma-Aldrich. Palmitic acid was coupled to fatty acid free Bovine Serum Albumin (BSA, Roche) to make a 6:1 BSA-palmitic acid conjugate solution, which is needed to dissolve palmitic acid in culture medium and therefore common practice in the field (reference Alsabeeh et al, Biochim. Biophys Acta. 2018 February; 1863(2): 143-151). Throughout this document this conjugate solution will be abbreviated as PA.

Figure 3:
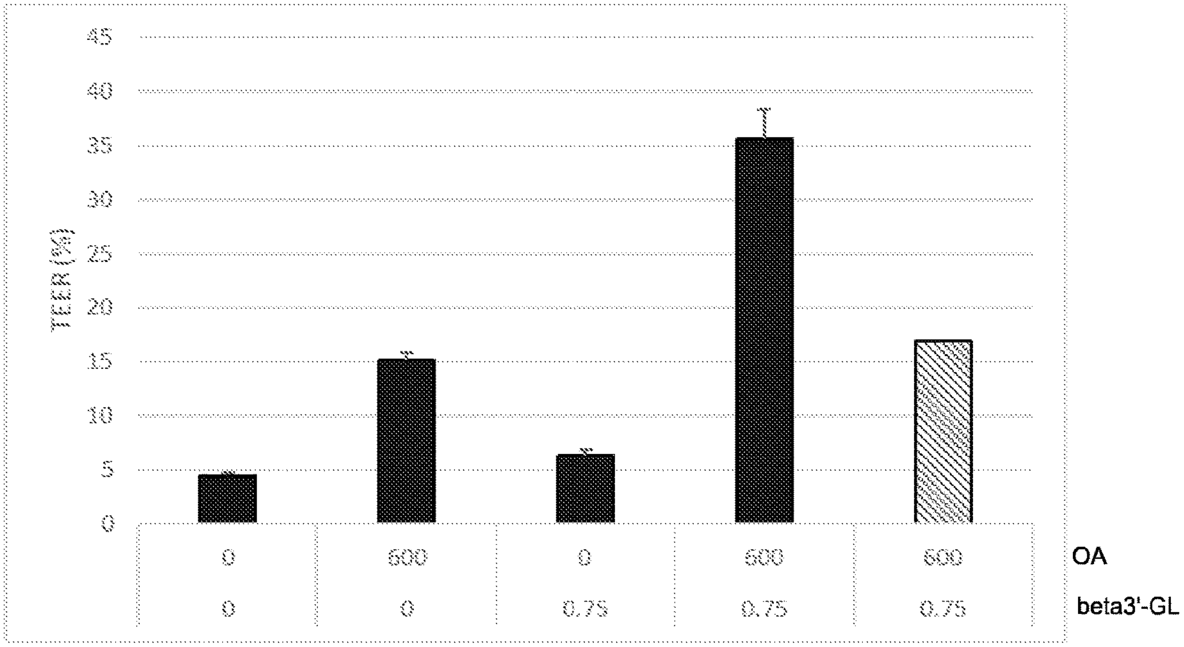
FIG. 3: Effect of OA, beta3'-GL and it combinations on the gut barrier function (TEER) in a model where the gut barrier is disrupted by DON. 0.75 wt % beta3'-GL, 600 μM OA and its combination were tested. The hatched bar gives the TEER as calculated based on the single ingredients beta3'-GL and OA.

The results are shown in Tables 5a and 5b and FIG. 3. Tables 5a and 5b show the effects of QOA and PA and beta3'-GL and its combinations on the intestinal barrier function as measured by TEER.

TABLE 5a

Effects of OA and beta3'-GL and its combination on the intestinal barrier function as measured by TEER (expressed relative to the medium control).

| beta3'GL (w/v %) | Oleic acid (µM) | % TEER (24 h) |
|---|---|---|
| 0 | 0 | 100 |
| 0 | 600 | 138 |
| 0.75 | 0 | 117 |
| 0.75 | 600 | 166*# |

*P < 0.05 compared with 0.0 control;.

#TEER expected based on single OA and beta3'GL effects: 155

TABLE 5b

Eeffects of PA and beta3'-GL and its combination on the intestinal barrier function as measured by TEER.

| 3'GL | Palmitic acid (µM) | % TEER (24 h) |
|---|---|---|
| 0 | 0 | 100 |
| 0 | 600 | 69 |
| 0.75 | 0 | 129 |
| 0.75 | 600 | 72# |

TEER expected based on single PA and beta3'GL effects: 98

As can be deduced from Tables 5a and 5b, addition of OA alone improved gut barrier function, whereas palmitic acid did not. Also addition of beta3'GL led to an improvement of the gut barrier function, in accordance with example 1. When a combination of OA and beta3'-GL was used, the gut barrier function improved significantly compared to the control without beta3'GL and OA and the value was higher than expected based on the additive effects of the single ingredients. The improving effect on TEER was also observed using 100 µM OA (data not shown), but was more pronounced with the 600 µM concentration.

No significant differences in TEER were observed in the experiments with PA, and the TEER was lower in the presence of PA. The combination of beta3'-GL and PA resulted in a TEER value that was lower than expected based on the single ingredients, and beta3'-GL was not able to improve the TEER in the presence of PA. This effect on TEER was also observed using 100 µM PA (data not shown), but was more pronounced with the 600 µM concentration.

FIG. 3 shows the effects of OA, beta3'-GL and its combinations on the intestinal barrier function in a model wherein the barrier function is disrupted by DON (4.2 µM). As can be deduced from FIG. 3, in the presence of beta3'-GL or OA the TEER in the presence of DON was somewhat higher than in the control. When both beta3'-GL and OA were present the TEER was higher than the control (p=0.05). Interestingly the TEER was much higher (about 2.1 fold) than expected based on the single ingredients. Also using the LY assay the gut barrier function was highest in the presence of both OA and beta3'-GL and significantly higher than the control without OA and beta3'-GL (p<0.05) (data not shown).

Palmitic acid on the other hand did not improve the TEER in the presence of DON and also the combination of PA and beta3'-GL did not result in an significantly improved barrier function compared to the control. A similar effect was observed with the LYF assay. (data not shown).

These results are indicative for the specific and synergistic effect of the combination of oleic acid and beta3'-GL (herein also referred to as beta 1,3'-galactosyllactose or Gal (beta 1-3)-Gal (beta 1-4)-Glc) on protecting the intestinal epithelial barrier function, in particular under conditions of challenges. This effect is specific for oleic acid as it was not observed with palmitic acid. Therefore it is advantageous to have a composition with beta3'-GL and a fat blend that is low in palmitic acid and high in oleic acid.

Example 6: Infant Formula

An infant formula, provided as a powder in a pack with instructions to reconstitute with water to a ready to drink milk. When reconstituted the formula contains per 100 ml:

68 kcal
about 1.4 g protein (mainly whey protein and casein from bovine) [casein/whey protein 1:1]
about 3.2 g lipid, (a combination of high oleic sunflower oil, coconut oil, canola oil, sunflower oil, fish oil, *Mortierella* alpine oil and soy lecithin) wherein the amount of fatty acids based on total fatty acids is
  PA 6.57, of which about 93 wt. % is located in the sn1,3 position
  SA 2.93
  OA 49.8
  LA 14.3
  ALA 1.71
  ARA 0.52
  EPA 0.11
  DHA 052
about 8.1 g digestible carbohydrates (mainly lactose)
about 825 mg non-digestible oligosaccharides, comprising about 745 mg galacto-oligosaccharides, of which about 25 mg beta3'-GL (sources Vivinal GOS and GOS produced by the betagalactosidase from *S. thermophilus* CNCM-1-1620) and about 80 mg IcFOS (source RaftilinHP)
minerals, trace elements, vitamins and other micronutrients as known in the art and according to international directives for infant formula.

Example 7: Follow on Formula

A follow on formula, provided as a powder in a pack with instructions to reconstitute with water to a ready to drink milk. When reconstituted the formula contains per 100 ml:

68 kcal
about 1.4 g protein (mainly whey protein and casein from bovine) [casein/whey protein 6:4]
about 3.2 g lipid, (a combination of high oleic sunflower oil, coconut oil, canola oil, sunflower oil, fish oil, *Mortierella* alpine oil and soy lecithin) wherein the amount of fatty acids based on total fatty acids is (wt. %):
  PA 6.51, of which about 93 wt. % is located in the sn1,3 position
  SA 2.92
  OA 49.9
  LA 14.3
  ALA 1.72
  ARA 0.29
  EPA 0.12
  DHA 0.56
about 8.1 g digestible carbohydrates (mainly lactose)
about 815 mg non-digestible oligosaccharides, comprising about 735 mg galacto-oligosaccharides, of which about 15 mg beta3'-GL (sources Vivinal GOS and GOS produced by the betagalactosidase from *S. thermophilus* CNCM-1-1620) and about 80 mg IcFOS (source RaftilinHP)
minerals, trace elements, vitamins and other micronutrients as known in the art and according to international directives for infant formula.

The invention claimed is:

1. A nutritional composition comprising:
at least 45 wt. % oleic acid based on total fatty acids,
no more than 10 wt. % palmitic acid based on total fatty acids,
a wt/wt ratio of palmitic acid:oleic acid of no more than 1:4.5, and
at least 0.05 wt. % beta1,3'-galactosyllactose based on total dry weight of the composition.

2. The nutritional composition according to claim 1, comprising at least 1.5 wt. % galacto-oligosaccharides based on total dry weight of the composition, wherein the amount of galacto-oligosaccharides includes the amount of beta1, 3'-galactosyllactose.

3. The nutritional composition according to claim 1, which is an infant formula, a follow on formula or a young child formula.

4. The nutritional composition according to claim 1, wherein the composition further comprises long chain fructo-oligosaccharides.

5. The nutritional composition according to claim 1, wherein the composition further comprises docosahexanoic acid, arachidonic acid and/or eicosapentaenoic acid, wherein the sum of docosahexaenoic acid, arachidonic acid and eicosapentaenoic acid is at least 0.8 wt. % based on total fatty acids.

6. The nutritional composition according to claim 1, wherein the sum of stearic acid and palmitic acid is less than 12 wt. % based on total fatty acids.

7. The nutritional composition according to claim 1, that comprises:
3 to 10 wt. % palmitic acid based on total fatty acids,
45 to 60 wt. % oleic acid based on total fatty acids,
a wt/wt ratio of palmitic acid:oleic acid in the range of 1:10 to 1:4.5, and
at least 0.05 wt. % beta1,3'-galactosyllactose based on total dry weight of the composition.

8. The nutritional composition according to claim 7 that comprises 1.5 wt. % to 10.9 wt. % galacto-oligosaccharides based on total dry weight of the composition, wherein the amount of galacto-oligosaccharides includes the amount of beta1,3'-galactosyllactose.

9. The nutritional composition according to claim 1, that comprises:
3 to 7 wt. % palmitic acid based on total fatty acids,
48 to 55 wt. % oleic acid based on total fatty acids,
a wt/wt ratio of palmitic acid:oleic acid in the range of 1:8 to 1:7, and
at least 0.10 wt. % beta1,3'-galactosyllactose based on total dry weight of the composition.

10. The nutritional composition according to claim 9 that comprises 2.2 wt. % to 5.8 wt. % galacto-oligosaccharides based on total dry weight of the composition, wherein the amount of galacto-oligosaccharides includes the amount of beta1,3'-galactosyllactose.

11. The nutritional composition according to claim 1, wherein the galacto-oligosaccharides are obtained by treating lactose with a beta-galactosidase from *S. thermophilus*.

12. A method for improving intestinal barrier function in a subject in need thereof, wherein the method comprises administering the nutritional composition according to claim 1 to the subject.

13. The method according to claim 12, wherein the method is for the prevention and/or treatment of intestinal barrier disruption.

14. The method according to claim 13, wherein the method is for treating and/or preventing an intestinal barrier mediated disorders selected from the group consisting of intestinal inflammation, infections originating from the intestine and food allergy.

* * * * *